US012558383B2

(12) United States Patent
Geng

(10) Patent No.: US 12,558,383 B2
(45) Date of Patent: Feb. 24, 2026

(54) AMERICAN COCKROACH EXTRACT, PREPARATION THEREOF, PREPARATION METHODS THEREFOR AND APPLICATIONS THEREOF

(71) Applicant: SICHUAN GOOD DOCTOR PANXI PHARMACEUTICAL CO., LTD, Xichang (CN)

(72) Inventor: Yuefei Geng, Sichuan (CN)

(73) Assignee: SICHUAN GOOD DOCTOR PANXI PHARMACEUTICAL CO., LTD, Xichang (CN)

( * ) Notice: Subject to any disclaimer, the term of this patent is extended or adjusted under 35 U.S.C. 154(b) by 713 days.

(21) Appl. No.: 17/762,951

(22) PCT Filed: Oct. 10, 2020

(86) PCT No.: PCT/CN2020/120079
§ 371 (c)(1),
(2) Date: Mar. 23, 2022

(87) PCT Pub. No.: WO2021/068909
PCT Pub. Date: Apr. 15, 2021

(65) Prior Publication Data
US 2022/0339205 A1     Oct. 27, 2022

(30) Foreign Application Priority Data
Oct. 11, 2019     (CN) .......................... 201910961501.9

(51) Int. Cl.
A61K 36/00       (2006.01)
A61K 35/64       (2015.01)
A61K 47/10       (2017.01)
A61K 47/12       (2006.01)

(52) U.S. Cl.
CPC .............. *A61K 35/64* (2013.01); *A61K 47/10* (2013.01); *A61K 47/12* (2013.01)

(58) Field of Classification Search
None
See application file for complete search history.

(56) References Cited

U.S. PATENT DOCUMENTS

2013/0052273 A1     2/2013   Geng

FOREIGN PATENT DOCUMENTS

| CN | 87100537 | A | 8/1988 |
| CN | 1548058 | A | 11/2004 |
| CN | 1943600 | A | 4/2007 |
| CN | 101502534 | A | 8/2009 |
| CN | 105878292 | A | 8/2016 |
| CN | 106074614 | A | 11/2016 |
| CN | 107753535 | A | 3/2018 |
| CN | 109966319 | A | 7/2019 |

OTHER PUBLICATIONS

Zhu et al. (2018) Molecules 23, 101 (11 pages) (Year: 2018).*
Siddiqui et al. (2023) Applied Entomology and Zoology 58: 1-11. (Year: 2023).*
Zhao et al. (2017) Chin. Med. 12: 26 (6 pages). (Year: 2017).*
International Search Report for Corresponding International Application No. PCT/CN2020/120079 dated Dec. 30, 2020 with English Translation (7 Pages).

* cited by examiner

*Primary Examiner* — Russell G Fiebig
(74) *Attorney, Agent, or Firm* — LUCAS & MERCANTI, LLP

(57)     ABSTRACT

The present application relates to the technical field of medicine, and in particular to *Periplaneta americana* L. extract, a preparation thereof, a preparation method and application thereof. The method for preparing *Periplaneta americana* L. extract includes the steps: 1) soaking fresh *Periplaneta americana* L. extract with ethanol; 2) reflux extracting with ethanol, and then filtering and combining the filtrates; and 3) concentrating the filtrate into *extractum*. The method uses environmental protection reagents such as ethanol, increases the content of bioactive substances of *Periplaneta americana* L. extract, saves time, human and material resources, saves energy and reduces production cost. The *Periplaneta americana* L. extract obtained by the present method has better anti-inflammatory activity and higher content of amino acids.

34 Claims, 7 Drawing Sheets

1

AMERICAN COCKROACH EXTRACT, PREPARATION THEREOF, PREPARATION METHODS THEREFOR AND APPLICATIONS THEREOF

CROSS-REFERENCE TO RELATED APPLICATIONS

This application is a 371 of PCT/CN2020/120079, filed Oct. 10, 2020, which claims the benefit of Chinese Patent Application No. 201910961501.9, filed Oct. 11, 2019.

TECHNICAL FIELD

The present application relates to the field of medicine, and in particular, to an extract of *Periplaneta americana* L., a preparation, a preparation method and use thereof.

BACKGROUND ART

*Periplaneta americana* L., an insect in *Periplaneta* of Blattodea, also known as "*blattaria*" or commonly known as "cockroach", has always been regarded as a pest. Although it has been killed by human beings by various means, it still survives tenaciously until now. According to textual research, *Periplaneta americana* L. has lived on the earth for more than 300 million years. With the movement and change of the earth's crust and the change of climate and environment, many species have become extinct, but cockroaches are showing stronger and stronger survival adaptability, which does show its tenacious vitality. As a drug application, *Periplaneta americana* L. has been included in China's earliest pharmaceutical monograph, that is, Sheng Nong's herbal classic, which has a history of more than 2000 years. In the book, it is listed as a medium-grade, saying that it "tastes salty and cold, cures blood stasis, alleviates cold and fever, and cures indigestion, laryngopharyngeal closure, internal cold and childless". A Supplement to Compendium of *Materia Medica* wrote: an infantile malnutrition, in spite of its severity (or even causing dying), can be effectively cured by eating cockroaches obtained from a kitchen and baked to dry. The patient can only smell the fragrance of the cockroaches, but not a fishy odor. Eating cockroaches for one or two times is enough for completely curing the patient, without failing. After curing, the patient becomes well-developed and white. This has been proved to be successful in every test. It can be seen that, *blattaria* has been used as medicine and food for a long time. It has been clinically proved that *Periplaneta Americana* has the functions of dispersing blood stasis, curing indigestion, detoxifying, clearing damp, reducing swelling, etc.

Due to the increase of clinical dosage in recent years, artificial breeding of *Periplaneta americana* L. has gradually sprung up in the South and North of China, and there is a GAP standard feeding plant, which can produce *Periplaneta americana* L. as medicinal materials, drugs and green organic food that meet standards for drugs and foods.

In the process of actual production and preservation of *Periplaneta americana* L., the fresh insects of *Periplaneta americana* L. are easy to rot, deteriorate and stink in 2-3 days, so that they cannot be used. In order to preserve *Periplaneta americana* L., manufacturers usually treat the insect bodies into dry insects by means of freeze-drying or heating drying. However, whether freezing or high-temperature drying will waste energy, manpower and material resources and time, and further destroy many bioactive substances, which is not conducive to subsequent preparation of products.

It is still necessary to further study and improve the extraction and preparation method of *Periplaneta americana* L., so as to make more effective use of *Periplaneta americana* L. and obtain better extract thereof. Direct extraction of *Periplaneta americana* L. fresh body is undoubtedly a relatively good method. At present, there is no relevant report on how to extract fresh body of *Periplaneta americana* L. more effectively.

SUMMARY

The inventor accidentally obtained a good fresh-keeping method of *Periplaneta americana* L. fresh body in a large number of experiments, which solves the problems in the prior art. The fresh-keeping means described herein can preserve the fresh body of *Periplaneta americana* L. for a long time and improve the bioactive substances contained therein.

Therefore, on one hand, the present application provides a method for preparing *Periplaneta americana* L. extract, which includes the following steps:

1) soaking fresh *Periplaneta americana* L. in ethanol;

2) reflux extracting by ethanol, and then filtering and combining obtained filtrates; and 3) concentrating the filtrate into an *extractum*.

In the present application, as one of the embodiments, the concentration of ethanol used for soaking in step 1) is 20%-95%, preferably 25%-70%, more preferably 25%-45%, and most preferably 25%.

In the present application, as one of the embodiments, the soaking time in step 1) is 10-60 days, preferably 20-60 days, further preferably 20-40 days. As an example, the time can be 20, 21, 22, 23, 24, 25, 26, 27, 28, 29, 30, 31, 32, 33, 34, 35, 36, 37, 38, 39 or 40 days.

In the present application, as one of the embodiments, the temperature for soaking in step 1) is 20° C.-60° C., preferably 30° C.-50° C., and most preferably 40° C.

In the present application, as one of the embodiments, the amount of ethanol used in step 1) is 1.5-3.5 times the weight of fresh *Periplaneta americana* L. (i.e. 1.5-3.5 BV).

In the present application, as one of the embodiments, the concentration of ethanol in step 2) is 50%-80%, preferably 80%.

In the present application, as one of the embodiments, the amount of ethanol added in step 2) is 1.5-3.5 times the weight of fresh *Periplaneta americana* L. (i.e. 1.5-3.5 BV), preferably 1.5 times.

As one of the embodiments, in step 1), ethanol 1.5 times the weight of fresh insects has been added during soaking, and in step 2), ethanol 1.5 times the amount is added again for the first reflux.

In the present application, as one of the embodiments, the times for reflux in step 2) is 1-3 times.

In the present application, as one of the embodiments, in step 2), ethanol of 1.5 times the weight of fresh *Periplaneta americana* L. (1.5 BV) is added again for the first reflux; when the second or third reflux are conducted in step 2), the amount of ethanol added is 3 times the weight of fresh *Periplaneta americana* (3 BV).

In the present application, as one of the embodiments, the time for reflux in step 2) is 1-2 h.

In the present application, as one of the embodiments, the concentration in step 3) is reduced pressure concentration.

In the present application, as one of the embodiments, the temperature for reduced pressure concentration in step 3) is 60° C.-90° C.

In the present application, as one of the embodiments, the relative density of the *extractum* in step 3) at 60° C. is 1.04-1.08.

In another aspect, the present application provides an *Periplaneta americana* L. extract prepared by a method described above. As one of the embodiments, the content of free amino acids in the extract is 30-55%.

In another aspect, the present application provides a preparation containing the extract of *Periplaneta americana* L., and the preparation contains the extract of *Periplaneta americana* L. prepared by the method described above and excipients. In the present application, the excipient comprises a clarifying agent.

In the present application, as one of the embodiments, the clarifying agent is a composition of chitosan and gelatin; as one of the embodiments, chitosan is 1% chitosan solution; and as one of the embodiments, gelatin is 1% gelatin solution.

In the present application, as one of the embodiments, the ratio of chitosan to gelatin is 1:1-1:4, preferably 1:3-1:4, and most preferably 1:3.

In the present application, as one of the embodiments, the crude drug concentration in the clarification step is ⅓-1/11 g/ml, preferably ⅓-⅐ g/ml, and most preferably ⅓ g/ml.

Crude drug concentration refers to the mass or weight of fresh body of *Periplaneta americana* L. per milliliter. As an example, if the crude drug concentration is ⅓ g/ml, it means that ⅓g of fresh body of *Periplaneta americana* L. is prepared into 1 ml solution.

In the present application, as one of the embodiments, the amount of clarifying agent in the preparation is 0.2-1.0 ml/g crude drug, and preferably 0.2-0.6 ml/g crude drug.

In the present application, as one of the embodiments, the excipient further comprises a sweetener and a preservative.

In the present application, as one of the embodiments, the sweetener includes but not limited to glycerol, cyclamate, aspartame or stevioside, preferably glycerol.

In the present application, as one of the embodiments, the preservative includes but not limited to hydroxyphenylalkyl esters (for example, Nipagins), benzoic acid, sodium benzoate, sorbic acid or potassium sorbate; and preferably potassium sorbate.

In the present application, as one of the embodiments, the amount of the sweetener is 5-20%.

In the present application, as one of the embodiments, the amount of the preservative is 0.05-0.3%.

In the present application, as one of the embodiments, the preparation is a traditional Chinese medicine mixture.

A further aspect of the present application further provides a method for preparing a preparation, which comprises the following steps: diluting *Periplaneta americana* L. extract with water, then heating to 100° C., cooling to 70° C., add clarifying agent under stirring, refrigerating, filtering, adding glycerol and potassium sorbate to the filtrate, finally adding remaining water, well mixing, filtering through a microporous filter membrane and sterilizing.

In the present application, as one of the embodiments, the method comprises: weighing fresh body of *Periplaneta americana* L., adding 25% ethanol 1.5 times(1.5 BV) the weight of the fresh body, sealing, standing at 40° C. for 20 days, taking out, reflux extracting with 80% ethanol for three times, wherein each extraction is performed for 1 h, 1.5 BV is added for the first extraction, 3.0 BV is added for the second and third extractions, filtering and combining the filtrates, recovering ethanol under reduced pressure at 65° C. and concentrating to a relative density of 1.04 (measured at 60° C.), adding water to 3 times the weight of fresh insects, well mixing, heating and boiling for 10 min, cooling down to 70° C., slowly adding clarifying agent, stirring, cooling, refrigerating overnight and filtering to obtain a clear solution of the fresh body of *Periplaneta americana* L.; then adding potassium sorbate and glycerol, well mixing, adding water, well mixing, filtering, and sterilizing at 115° C. for 40 min, and obtained.

The present application further provides an use of *Periplaneta americana* L. extract prepared by the present application or the present preparations for preparing drugs for anti-inflammatory.

One of the objects of the present application is to provide a method for preserving the fresh body of *Periplaneta americana* L. for a long time. The use of environmental protection reagents such as ethanol saves time, manpower and material resources, saves energy and reduces production cost. At the same time, it can increase the bioactive substances in *Periplaneta americana* L.

One of the objects of the invention is to provide a fresh-keeping agent for *Periplaneta americana* L., which is selected from one or more of water, ethanol, glycerol, propylene glycol, water-soluble chitosan and seaweed polysaccharide. It has been found by a large number of experiments that fresh body treated with preservatives have more bioactive substances than untreated fresh or dry insects.

Further, the preservative solution of *Periplaneta americana* L. is ethanol with a concentration of 10-90%.

One of the objects of the invention is to provide a fresh-keeping method for *Periplaneta americana* L., which is characterized in that *Periplaneta americana* L. is soaked in one or more substances including ethanol, propylene glycol, glycerol, water-soluble chitosan and seaweed polysaccharide.

Further, it is characterized in that *Periplaneta americana* L. is soaked in ethanol with a concentration of 10-90%.

Further, 25-60% ethanol is used to soak *Periplaneta americana* L.

Further, the time for soaking *Periplaneta americana* L. is 10 days or longer.

Further, the temperature for soaking *Periplaneta americana* L. is 20-60° C.

Further, in the fresh-keeping method of *Periplaneta americana* L., the amount of ethanol for soaking is 1.5-3.5 times the weight of fresh body (1.5-3.5 BV).

The present application has the advantages that, the present application can preserve the fresh body of *Periplaneta americana* L. for a long time, without the need of freeze-drying or drying. Meanwhile, it can increase the bioactive substances in the medicinal materials of *Periplaneta americana* L. The use of ethanol and other environmental protection reagents saves time, manpower and material resources, saves energy and reduces production costs. The extract of *Periplaneta americana* obtained by the invention has better anti-inflammatory activity and higher content of amino acids.

US 12,558,383 B2

5

Figure 3:
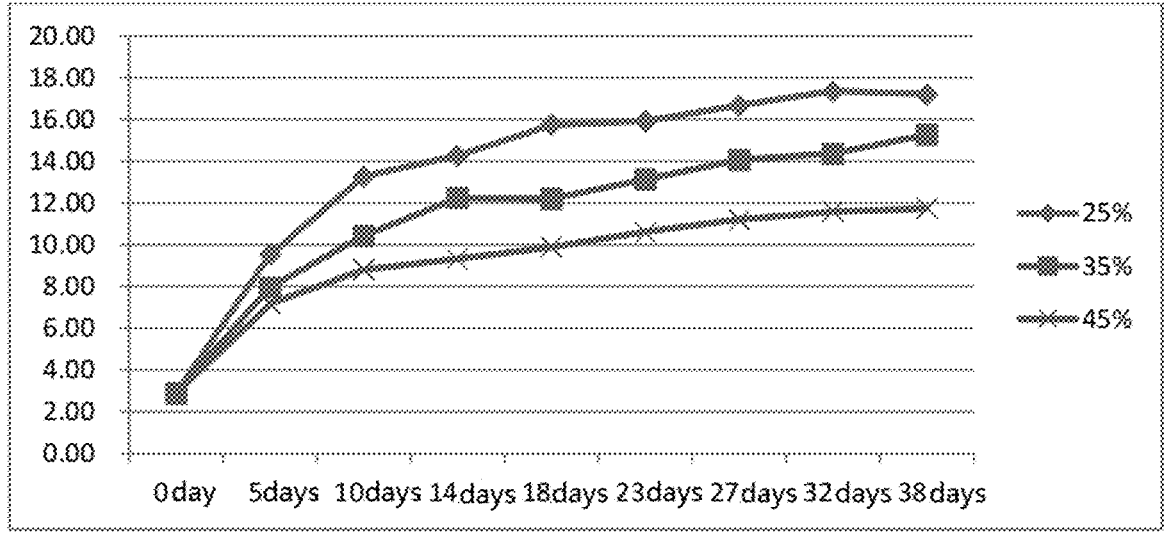

FIG. 3: effects of different ethanol concentrations and soaking time on total solids in Test Example 1.

Figure 4:
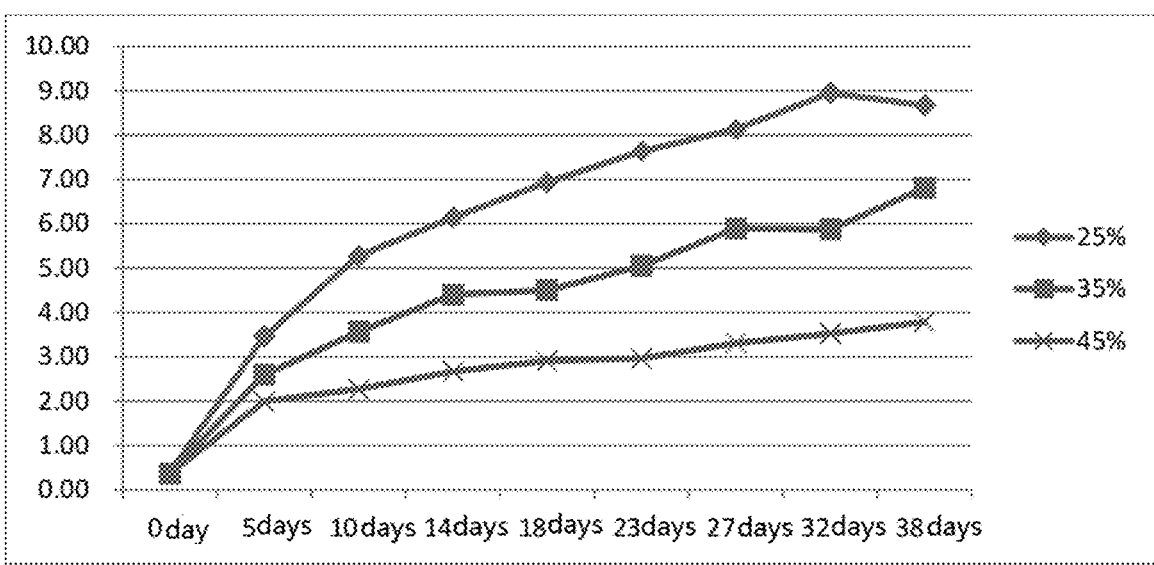

FIG. 4: effects of different ethanol concentrations and soaking time on free amino acids in Test Example 1.

Figure 5:
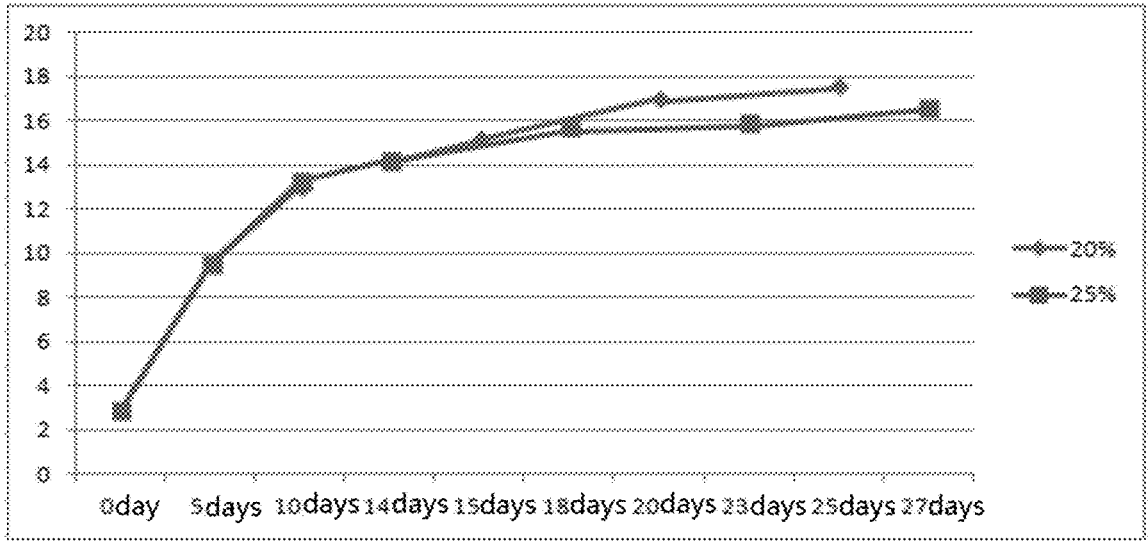

FIG. 5: effects of different ethanol concentrations and soaking time on water-soluble total solids in Test Example 1.

Figure 6:
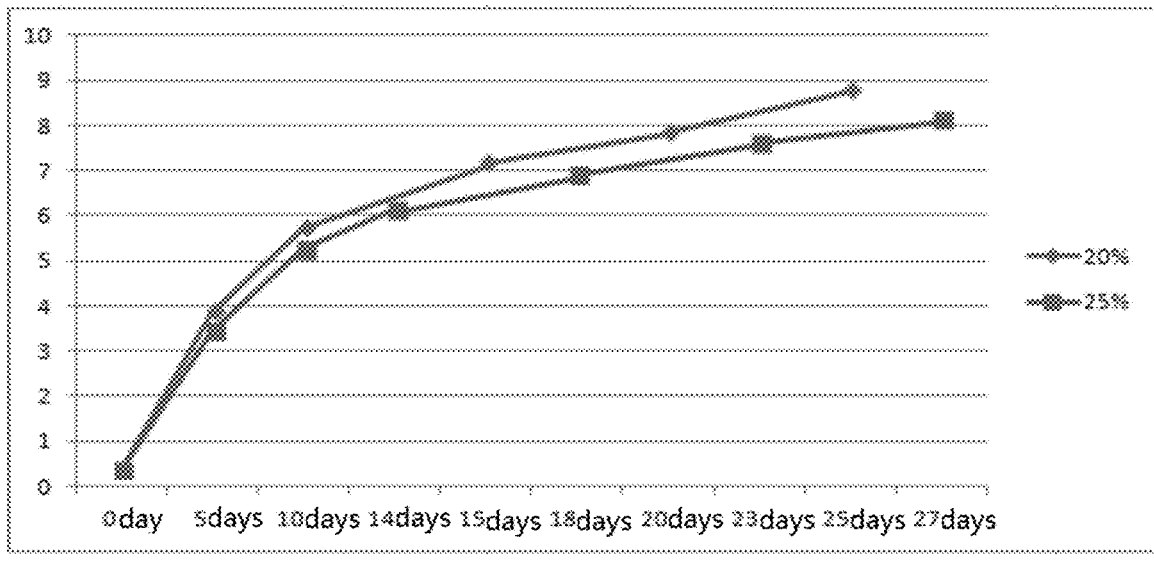

FIG. 6: effects of different ethanol concentrations and soaking time on free amino acids in Test Example 1.

Figure 7:
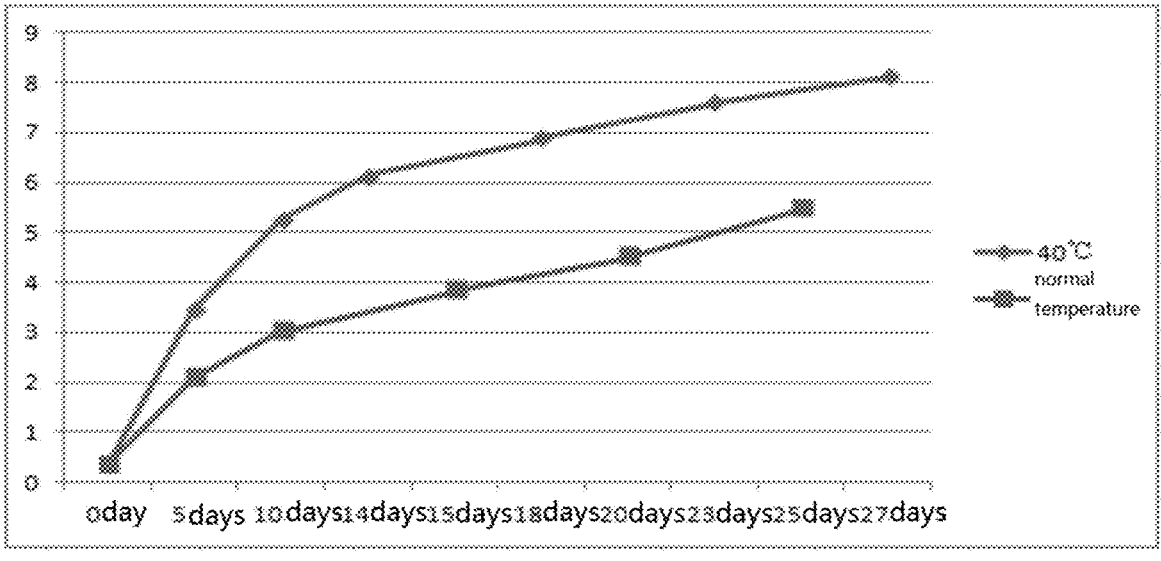

FIG. 7: variation trend diagram of free amino acid yield as a function of time in normal temperature group and 40° C. group in Test Example 1.

Figure 8:
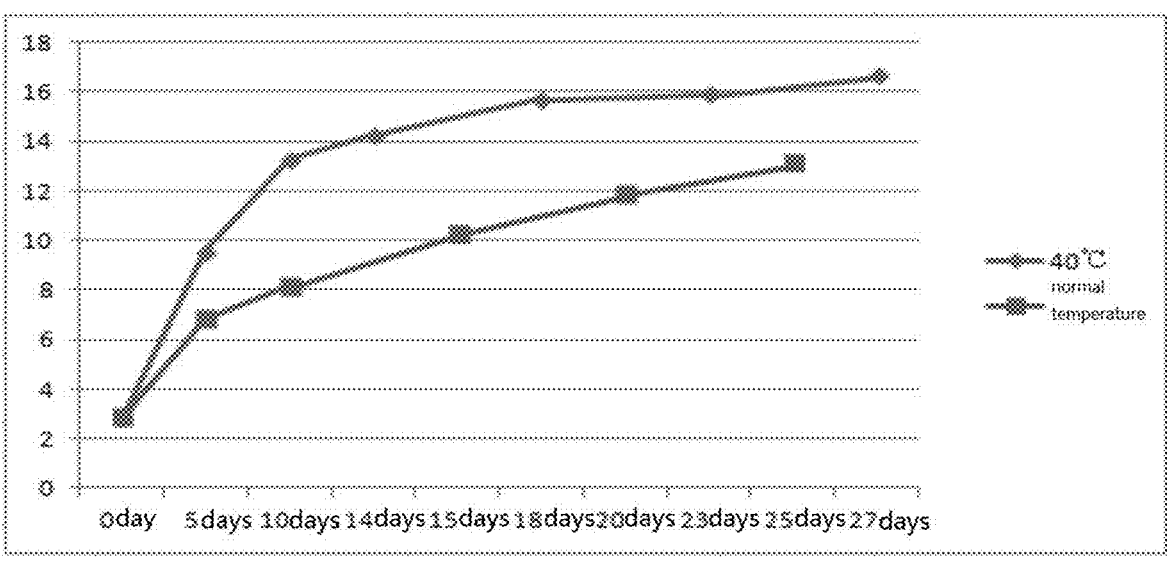

FIG. 8: variation trend diagram of water-soluble total solids as a function of time in normal temperature group and 40° C. group in Test Example 1.

Figure 9:
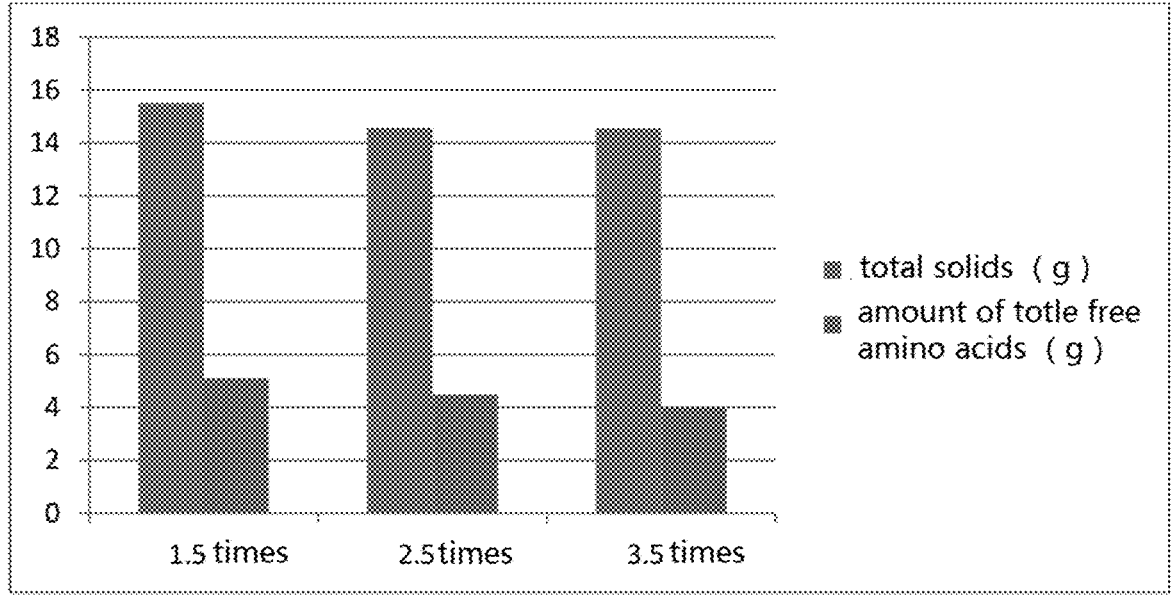

FIG. 9: investigation results of different ethanol immersion times in Test Example 1.

Figure 10:
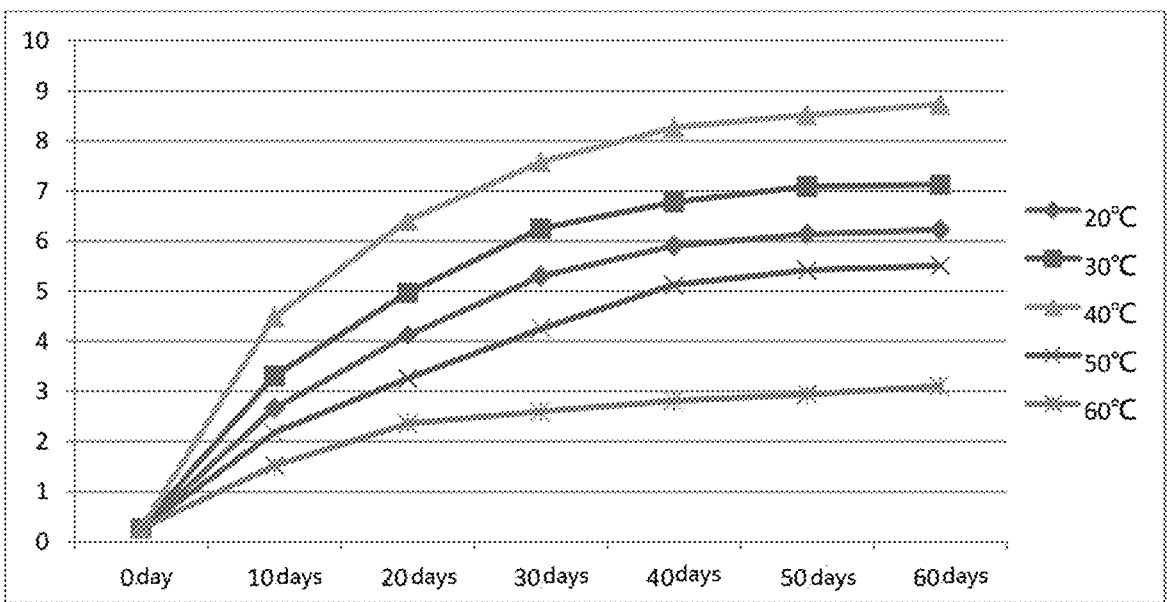

FIG. 10: variation trend diagram of total free amino acids in Test Example 1.

Figure 11:
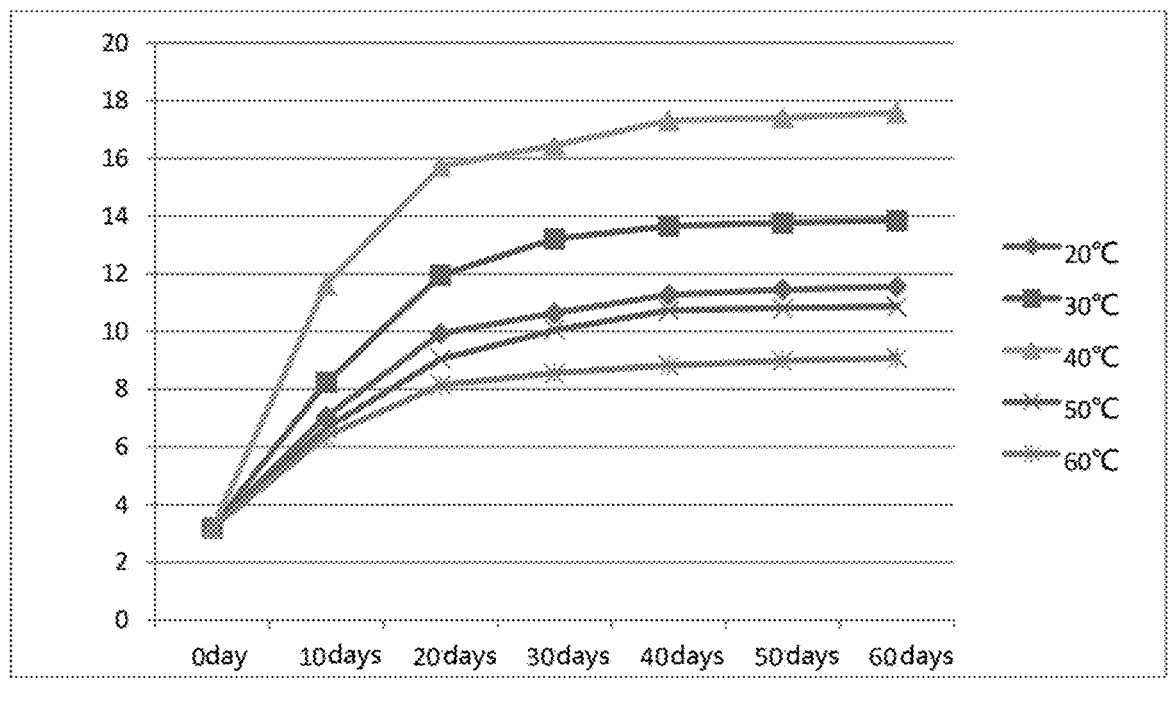

FIG. 11: variation trend diagram of water-soluble total solids in Test Example 1 in Test Example 1.

Figure 12:
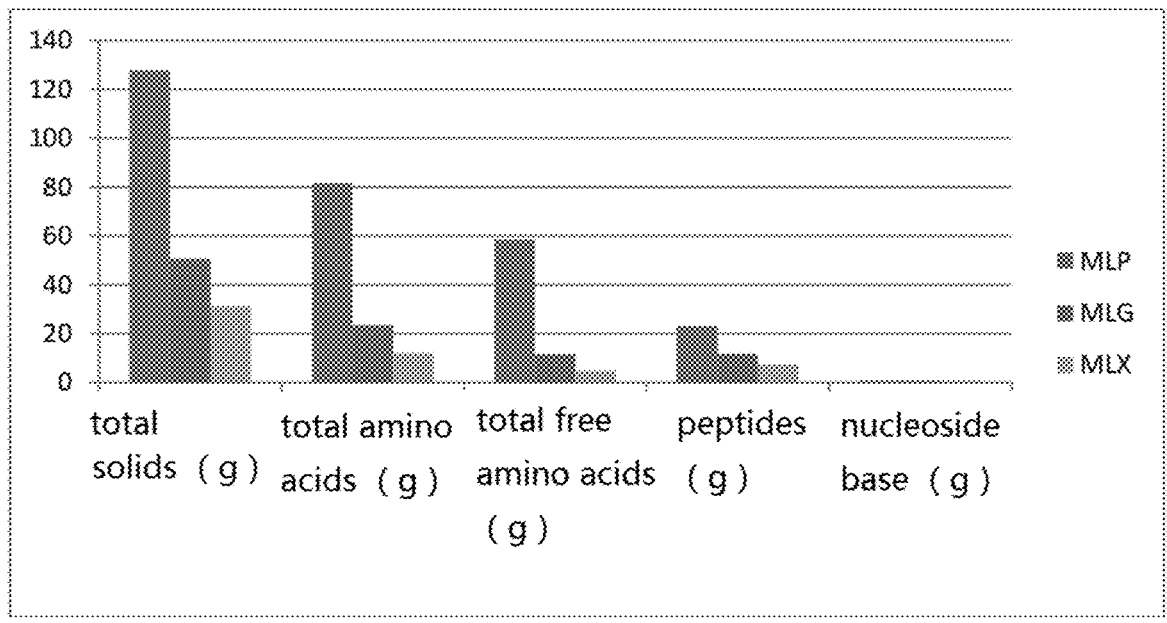

FIG. 12: comparison diagram of total amount of various substances in the three extracts in Test Example 1.

Figure 13:
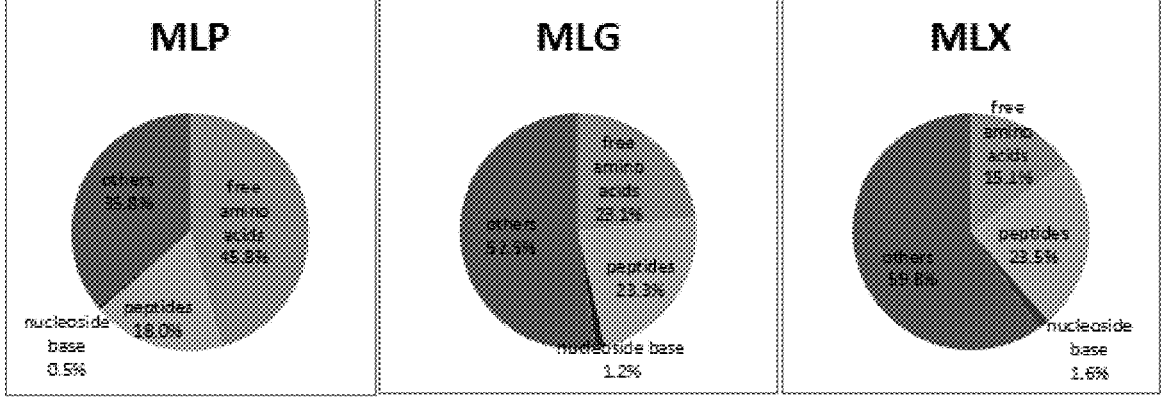

FIG. 13: pie chart of various substances in MLP, MLG and MLX samples in total solids in Test Example 1.

Figure 14:
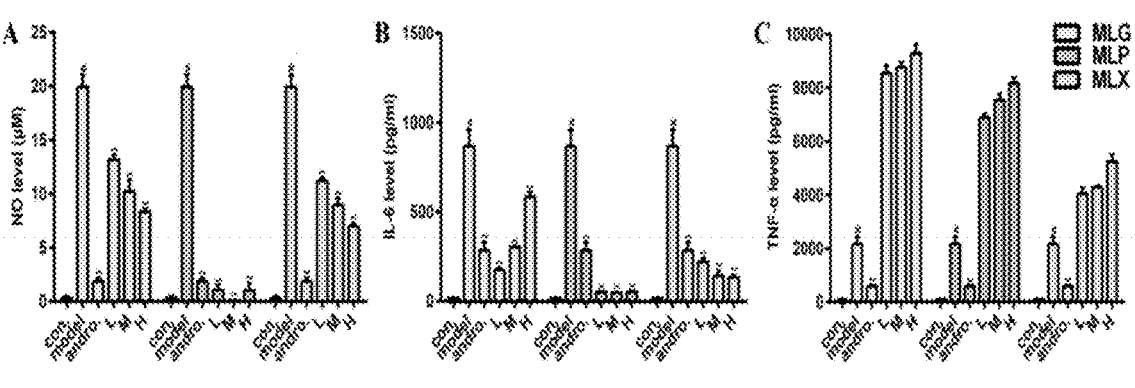

FIG. 14: effect on the amount of secretion of TNFa, IL-6 and NO of LPS inflammatory-inducing cells by MLG, MLP and MLX in Test Example 1 (x̄±s, n=3), where con. represents the blank group, model represents the model group, and andro. represents the positive drug andrographolide group, L represents the low dosage group (in which the original drug solution is diluted by 160 times), M represents the medium dosage group (in which the original drug solution is diluted by 120 times), and H represents the high dosage group (in which the original drug solution is diluted by 80 times); since all drugs are measured at the same time, all drugs share the same blank, model and positive drug group data for a same index (compared with the control group, #P<0.01; compared with the model group, * P<0.05, * * P<0.01).

DETAILED DESCRIPTION

The present application is described in detail below through examples, but it does not mean imposing any adverse limitation to the present application. The present application has been described in detail, and its specific embodiments are also disclosed. It will be obvious to those skilled in the art to make various changes and improvements to the specific embodiments of the present application without departing from the spirit and scope of the present application.

Preparation of *Periplaneta americana* L. Extract

EXAMPLE 1

Fresh body of *Periplaneta americana* L. was added into 1.5 BV 25% ethanol, soaked at 40° C.±2° C. for 20-40 days, refluxed with 80% ethanol for three times, in which each reflux was performed for 1 hour, and ethanol was added by 1.5 times, 3.0 times and 3.0 times for each reflux, respectively. The solution was filtered. Ethanol was recovered at 60-90° C. and the solution was concentrated to obtain a thin *extractum* with a relative density of 1.04-1.08 (measured at 60° C.).

6

EXAMPLE 2

Fresh body of *Periplaneta americana* L. was weighed by 1000 g/portion, placed in a glass bottle, added with 1500 ml of 25% ethanol, sealed, left to stand at 40° C. for 20 days, taken out, extracted with 80% ethanol for 3 times, in which each extraction was performed for 1 h, and the ethanol was added by 1.5 BV (1.5 L) for the first time, and by 3.0 BV (3.0 L) for the second and third times, and filtered. The filtrates were combined. Ethanol was recovered under reduced pressure at 65° C. and the solution was concentrated to a relative density of 1.06 (60° C.), and obtained.

EXAMPLE 3

1000 g Fresh body of *Periplaneta americana* L. was weighed, placed in a glass bottle, added with 4500 ml 50% ethanol, sealed, left to stand at 40° C. for 60 days, taken out, refluxed with 5000 ml 50% ethanol for 2 h to extract, and filtered. Ethanol was recovered under reduced pressure at 90° C. and the solution was concentrated to a relative density of 1.08 (60° C.).

EXAMPLE 4

1000 g Fresh body of *Periplaneta americana* L. was weighed, placed in a glass bottle, added with 1500 ml 20% ethanol, sealed, left to stand at 20° C. for 10 days, taken out, extracted with 80% ethanol for 3 times, in which each extraction was performed for 1 h, and the ethanol was add by 1.5 BV (1.5 L) for the first time, and by 3.0 BV (3.0 L) for the second and third times, and filtered. The filtrates were combined. Ethanol was recovered under reduced pressure at 60° C. and the solution was concentrated to a relative density of 1.04 (60° C.), and obtained.

EXAMPLE 5

1000 g Fresh body of *Periplaneta americana* L. was weighed, placed in a glass bottle, added with 2000 ml 90% ethanol, sealed, left to stand at 50° C. for 60 days, taken out, extracted with 70% ethanol for 3 times, in which each extraction was performed for 1.5 h, and the ethanol was add by 2 BV (2 L) for the first time, and by 4.0 BV (4.0 L) for the second and third times, and filtered. The filtrates were combined. Ethanol was recovered under reduced pressure at 70° C. and the solution was concentrated to a relative density of 1.07 (60° C.), and obtained.

EXAMPLE 6

2000 g Fresh body of *Periplaneta americana* L. was weighed, placed in a glass bottle, added with 7000 ml 30% ethanol, sealed, left to stand at 30° C. for 40 days, taken out, extracted with 60% ethanol for 3 times, in which each extraction was performed for 1 h, and the ethanol was add by 0.5 BV (1.0 L) for the first time, and by 4.0 BV (8.0 L) for the second and third times, and filtered. The filtrates were combined. Ethanol was recovered under reduced pressure at 60° C. and the solution was concentrated to a relative density of 1.05 (60° C.), and obtained.

EXAMPLE 7

1500 g Fresh body of *Periplaneta americana* L. was weighed, placed in a glass bottle, added with 3000 ml 25% ethanol, sealed, left to stand at 35° C. for 45 days, taken out, extracted with 80% ethanol for 3 times, in which each extraction was performed for 1.5 h, and the ethanol was add by 2.0 BV (3.0 L) for the first time, and by 4.0 BV (6.0 L) for the second and third times, and filtered. The filtrates were combined. Ethanol was recovered under reduced pressure at 80° C. and the solution was concentrated to a relative density of 1.07 (60° C.), and obtained.

Preparation of *Periplaneta americana* L. Extract Mixture

Preparation of a Clarifying Agent

1% gelatin solution: 3 g gelatin was weighed, soaked in 150 ml purified water for 30 min, then added with 150 ml hot water (>95° C.) under stirring until gelatin was completely dissolved, and cooled, and obtained.

1% chitosan solution: 1 g chitosan was weighed, added to 100 ml purified water, stirred evenly, and slowly added with 1 ml glacial acetic acid under stirring until chitosan was completely dissolved, and obtained.

The clarifying agent solution: 1% gelatin solution and 1% chitosan solution were mixed by the ratio of 3:1, and obtained.

EXAMPLE 8

200 g fresh body of *Periplaneta americana* L. was added to 300 ml of 25% ethanol, placed at 40° C. (±2° C.) for 20-40 days, and reflux extracted with 80% ethanol for 3 times, in which each extraction was performed for 1 h, and the ethanol was add by 300 ml for the first time, and by 600 ml for the second and third times, respectively, and filtered. Ethanol was recovered under reduced pressure at 50-100° C. and the solution was concentrated to obtain a thin *extractum* with a relative density of 1.04-1.08 (measured under 60° C.). The thin *extractum* was added water to 600 ml, boiled for 10-30 min, cooled to 60-70° C., added with 40-120 ml of the clarifying agent prepared by evenly mixing 1% gelatin solution and 1% chitosan solution by the ratio of 3:1, mixed evenly, left to stand at 1-8° C. for 16-48 h, filtered, added with 150 g glycerol and 1 g potassium sorbate, added with water to 1000 ml, mixed evenly, filtered, bottled, and sterilized at 116° C. (±2° C.) for 40 minutes, and obtained.

EXAMPLE 9

Fresh body of *Periplaneta americana* L. was weighed by 1000 g/portion, placed in a glass bottle, added with 1500 m125% ethanol, sealed, left to stand at 40° C. for 20 days, taken out, extracted with 80% ethanol for 3 times, in which each extraction was performed for 1 h, and the ethanol was add by 1.5 BV (1.5 L) for the first time, and by 3.0 BV (3.0 L) for the second and third times, and filtered. The filtrates were combined. Ethanol was recovered under reduced pressure at 65° C. The solution was concentrated to a relative density of 1.06 (60° C.), cooled, added with water to 3000 ml, mixed evenly, boiled for 10 min, cooled down to 70° C., slowly added with 600 ml clarifying agent, stirred for 10 min, cooled, refrigerated overnight, and filtered to obtain a clear solution of the fresh body of *Periplaneta americana* L. A suitable amount of the clear solution (equivalent to 200 g fresh body) was taken, added with 1.0 g potassium sorbate and 150 g glycerol respectively, mixed evenly, added with water to 1000 ml, mixed evenly, filtered, bottled to 10 ml/bottle, and sterilized at 115° C. for 40 min.

Test Example 1 Investigation on the Conditions for Soaking Fresh Body of *Periplaneta americana* L 1) Investigation on Ethanol Concentration and Soaking Time Investigation on the soaking of fresh body at different ethanol concentrations including 20%, 50%, 70% and 95% ethanol Several 100 g portions of fresh body of *Periplaneta americana* L. were taken, added with 150 ml of 20%, 50%, 70% and 95% ethanol, respectively. They were kept at normal temperature, and reflux extracted with 4 BV, 3 BV, and 3 BV 70% ethanol, respectively, on day 0 (0 month), day 12 (0.5 month), day 31 (1.0 month), day 47 (1.5 month) and day 61 (2.0 month), respectively, and filtered. Ethanol was recovered from the filtrate under reduced pressure at 65° C., added with water to 500 ml for dissolving, and then centrifuged on a high-speed freezing centrifuge (10° C. 12000 r/min) for 30 min to obtain the supernatant, that is, the sample. The content of amino acids in the sample and the yield of water-soluble total solids were determined.

(The yield of water-soluble total solids was determined referring to the drying method in Pharmacopoeia 2015 Edition, and the content of total amino acids was determined by HPLC method after sample derivatization.) The test results are shown in Table 1 and Table 2.

TABLE 1

Content of amino acids in the sample

| concentration | time<br>content | | | | |
| --- | --- | --- | --- | --- | --- |
| | day 0 | day 12 | day 31 | day 47 | day 61 |
| 20% | 0.31 | 3.23 | 6.25 | 7.17 | 6.96 |
| 50% | 0.31 | 2.34 | 4.13 | 4.42 | 4.93 |
| 70% | 0.31 | 1.64 | 2.15 | 2.27 | 2.29 |
| 95% | 0.31 | 0.99 | 1.09 | 1.17 | 1.21 |

TABLE 2

Yield of water-soluble total solids in the sample

| concentration | time<br>yield | | | | |
| --- | --- | --- | --- | --- | --- |
| | day 0 | day 12 | day 31 | day 47 | day 61 |
| 20% | 2.23 | 9.44 | 13.55 | 15.43 | 14.61 |
| 50% | 2.23 | 6.98 | 10.43 | 10.75 | 11.5 |
| 70% | 2.23 | 6.09 | 7.13 | 7.51 | 7.49 |
| 95% | 2.23 | 4.52 | 5.49 | 5.64 | 5.43 |

Figure 1:
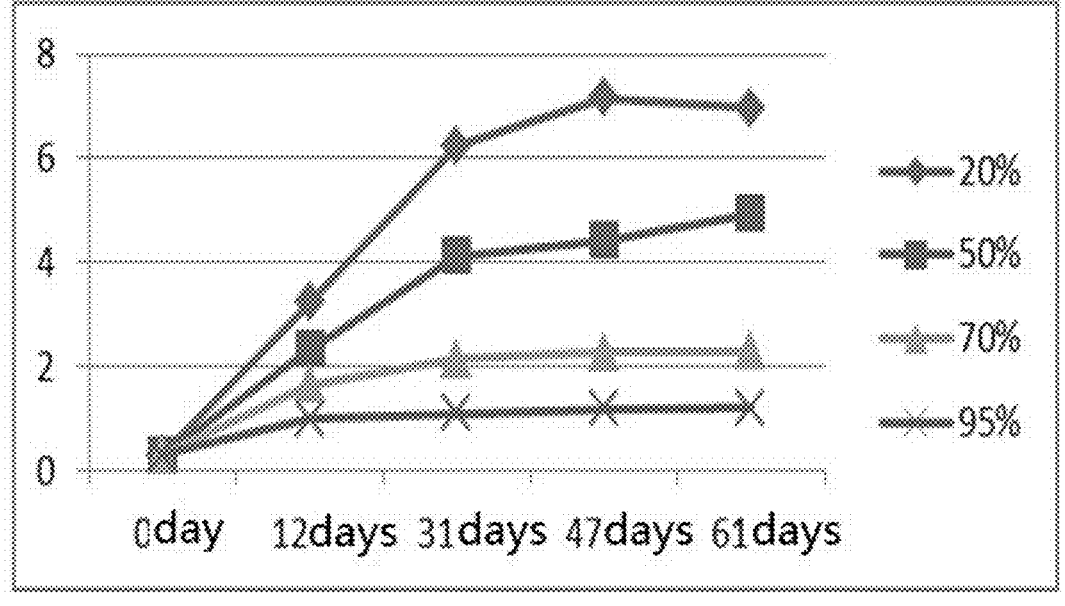
FIG. 1: effects of different ethanol concentrations and soaking time on total free amino acids in Test Example 1.
Figure 2:
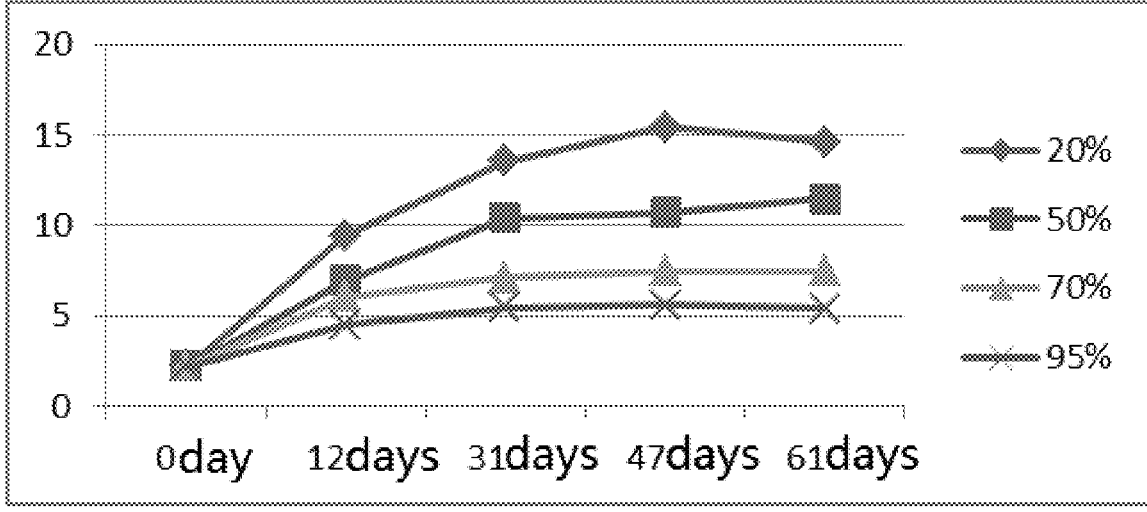
FIG. 2: effects of different ethanol concentrations and soaking time on the yield of water-soluble total solids in Test Example 1.

It can be seen from FIG. 1 and FIG. 2 that, the content of total amino acids and the yield of water-soluble total solids of fresh body of *Periplaneta americana* L. soaked in different concentrations of ethanol are increased in different degrees with the increase of soaking time. With the increase of ethanol concentration, the growth rate slowed down. In particular, soaking in 20% ethanol has the fastest growth rate and the largest growth. Soaking in 95% ethanol has the lowest growth rate and the smallest growth rate.

② Investigation on Soaking in 25%, 35% and 45% Ethanol

Several 100 g/portions of fresh body of *Periplaneta americana* L. were placed in a glass bottle, added with 150 ml of 25%, 35%, and 45% ethanol, respectively, sealed, and kept at 40° C. Part of the samples soaked in 25%, 35%, and 45% ethanol were taken out every 5 days, reflux extracted with 70% ethanol for three times, in which 250 ml of ethanol was added for the first extraction, and 300 ml of ethanol was added for the second and third times, and each extraction was performed for 1 h, and filtered. The filtrates were combined. Ethanol was recovered under reduced pressure at 65° C. until there was no smell of ethanol. The extract was cooled down, added with water to 500 ml, mixed evenly, and centrifuged (at 12000 r/min) for 30 min to obtain a supernatant. The supernatant was filtered, and the contents of free amino acids and water-soluble total solids were determined in the filtrate. The results are shown in Table. 3 and Table. 4.

③ Investigation on Soaking in 20% Ethanol.

Fresh body of *Periplaneta americana* L. was weighed by 100 g/portion, placed in a glass bottle, added with 150 ml of 20%, sealed, and left to stand for 25 days at 40° C. Part of the soaked samples were taken out every 5 days, reflux extracted with 70% ethanol for three times, in which 250 ml of ethanol was added for the first extraction, and 300 ml of ethanol was added for the second and third times, and each extraction was performed for 1 h, and filtered. The filtrates were combined. Ethanol was recovered under reduced pressure at 65° C. until there was no smell of ethanol. The extract

TABLE 3

| | Effect of different ethanol concentrations and soaking time on the total solids (n = 2) | | | | | | | | |
|---|---|---|---|---|---|---|---|---|---|
| Concentration of ethanol | Day 0 (g) | Day 5 (g) | Day 10 (g) | Day 14 (g) | Day 18 (g) | Day 23 (g) | Day 27 (g) | Day 32 (g) | Day 38 (g) |
| 25% | 2.87 | 9.53 | 13.28 | 14.27 | 15.74 | 15.92 | 16.67 | 17.36 | 17.21 |
| 35% | 2.87 | 7.96 | 10.43 | 12.24 | 12.20 | 13.13 | 14.07 | 14.37 | 15.27 |
| 45% | 2.87 | 7.18 | 8.81 | 9.33 | 9.89 | 10.62 | 11.21 | 11.59 | 11.74 |

According to the test results in Table 3, a variation trend diagram of the water-soluble solids as a function of time during soaking the fresh body of *Periplaneta americana* L. by 25%, 35% and 45% ethanol is plotted, in which the soaking time is the horizontal ordinate and the water-soluble total solids is the longitudinal ordinate, as shown in FIG. 3.

was cooled down, added with water to 500 ml, mixed evenly, and centrifuged (at 12000 r/min) for 30 min to obtain a supernatant. The supernatant was filtered, and the contents of free amino acids and water-soluble total solids were determined in the filtrate. The results are shown in Table. 5 and Table. 6.

TABLE 4

| | Effect of different ethanol concentrations and soaking time on free amino acids (n = 2) | | | | | | | | |
|---|---|---|---|---|---|---|---|---|---|
| Concentration of ethanol | Day 0 (g) | Day 5 (g) | Day 10 (g) | Day 14 (g) | Day 18 (g) | Day 23 (g) | Day 27 (g) | Day 32 (g) | Day 38 (g) |
| 25% | 0.37 | 3.46 | 5.27 | 6.14 | 6.93 | 7.63 | 8.13 | 8.95 | 8.67 |
| 35% | 0.37 | 2.59 | 3.56 | 4.40 | 4.50 | 5.05 | 5.89 | 5.87 | 6.80 |
| 45% | 0.37 | 1.99 | 2.27 | 2.67 | 2.91 | 2.96 | 3.30 | 3.52 | 3.78 |

According to the test results in Table 4, a variation trend diagram of the free amino acids as a function of time during soaking the fresh body of *Periplaneta americana* L. by 25%, 35% and 45% ethanol is plotted, in which the soaking time is the horizontal ordinate and the amount of free amino acids is the longitudinal ordinate, as shown in FIG. 4.

The results showed that the amount of water-soluble total solids and free amino acids increased significantly with the decrease of ethanol concentration, and was the highest in the 25% ethanol soaking group at each time node. Therefore, 25% ethanol was selected to soak the fresh body of *Periplaneta americana* L.

The results of 25% ethanol soaking group showed that the amount of water-soluble total solids and free amino acids increased significantly in the first 20 days than in the later period, and there was a relatively flat growth in 20-38 days. Therefore, the soaking time was preliminarily determined as 20-38 days.

The above results showed that, the lower the ethanol immersion concentration is, the higher the yields of water-soluble total solids and free amino acids are. For a comparative test with soaking in less than 25% ethanol and investigating the anti-corrosion problem during soaking, another group of fresh body of *Periplaneta americana* L. is soaked in 20% ethanol for the test.

TABLE 5

| Effect of 20% ethanol on free amino acids and water-soluble total solids (n = 2) | | | | | | |
|---|---|---|---|---|---|---|
| Evaluation indexes | Day 0 | Day 5 | Day 10 | Day 15 | Day 20 | Day 25 |
| Total solids (g) | 2.87 | 9.57 | 13.06 | 15.26 | 17.06 | 17.67 |
| Free amino acids (g) | 0.37 | 3.88 | 5.74 | 7.18 | 7.86 | 8.78 |

TABLE 6

| Effect of 25% ethanol on free amino acids and water-soluble total solids (n = 2) | | | | | | | |
|---|---|---|---|---|---|---|---|
| Evaluation indexes | 0 天 | 5 天 | 10 天 | 14 天 | 18 天 | 23 天 | 27 天 |
| Total solids (g) | 2.87 | 9.53 | 13.28 | 14.27 | 15.74 | 15.92 | 16.67 |
| Free amino acids (g) | 0.37 | 3.46 | 5.27 | 6.14 | 6.93 | 7.63 | 8.13 |

Note:
the data of this table is from Table 3 and Table 4.

According to the test results in Table 5 and Table 6, a variation trend diagram of the water-soluble solids as a function of time during soaking the fresh body of *Periplaneta americana* L. by 20% and 25% ethanol is plotted, in which the soaking time is the horizontal ordinate and the water-soluble total solids is the longitudinal ordinate, as shown in FIG. 5.

According to the test results in Table 5 and Table 6, a variation trend diagram of the free amino acids as a function of time during soaking the fresh body of *Periplaneta americana* L. by 20% and 25% ethanol is plotted, in which the soaking time is the horizontal ordinate and the free amino acids is the longitudinal ordinate, as shown in FIG. 6.

The above test results showed that the yield of water-soluble total solids and free amino acids have a similar increase in in the two groups, which are slightly higher in the 25% ethanol group. However, in the 20% ethanol group, it was found that the samples smelled and deteriorated after soaking the fresh body of *Periplaneta americana* L. for 20 days. Therefore, 25% ethanol was preliminarily selected to soak the fresh body of *Periplaneta americana* L. for 20-38 days.

2) Investigation on Soaking Temperature

Fresh body of *Periplaneta americana* L. was weighed by 100 g/portion, placed in a glass bottle, added with 150 ml of 25% ethanol respectively, sealed, and left to stand at 40° C. The soaked samples were taken out every 5 days, reflux extracted with 70% ethanol for three times, in which 250 ml of ethanol was added for the first extraction, and 300 ml of ethanol was added for the second and third times, and each extraction was performed for 1 h, and filtered. The filtrates were combined. Ethanol was recovered under reduced pressure at 65° C. until there was no smell of ethanol. The extract was cooled down, added with water to 500 ml, mixed evenly, and centrifuged (at 12000 r/min) for 30 min to obtain a supernatant. The supernatant was filtered, and the contents of free amino acids and water-soluble total solids were determined in the filtrate. The results are shown in Table. 7 and Table. 8.

TABLE 7

Effect of soaking the fresh body at 40° C. on the amount of obtained free amino acids and water-soluble total solids (n = 2)

| Evaluation indexes | Day 0 | Day 5 | Day 10 | Day 14 | Day 18 | Day 23 | Day 27 |
|---|---|---|---|---|---|---|---|
| Total solids (g) | 2.87 | 9.53 | 13.28 | 14.27 | 15.74 | 15.92 | 16.67 |
| Free amino acids (g) | 0.37 | 3.46 | 5.27 | 6.14 | 6.93 | 7.63 | 8.13 |

Note:
the data of this table is from Table 3 and Table 4.

TABLE 8

Effect of soaking the fresh body at normal temperature on the amount of obtained free amino acids and water-soluble total solids (n = 2)

| Evaluation indexes | Day 0 | Day 5 | Day 10 | Day 15 | Day 20 | Day 25 |
|---|---|---|---|---|---|---|
| Total solids (g) | 2.87 | 6.83 | 8.16 | 10.26 | 11.88 | 13.14 |
| Free amino acids (g) | 0.37 | 2.10 | 3.04 | 3.86 | 4.55 | 5.50 |

According to the test results in Table 7 and Table 8, a variation trend diagram of the yield of the amino acids as a function of time is plotted, in which the soaking time is the horizontal ordinate and the amount of obtained amino acids is the longitudinal ordinate, as shown in FIG. 7.

According to the test results in Table 7 and Table 8, a variation trend diagram of the water-soluble total solids as a function of time is plotted, in which the soaking time is the horizontal ordinate and the water-soluble total solids is the longitudinal ordinate, as shown in FIG. 8.

The above test results show that the yields of water-soluble total solids and free amino acids in the normal temperature group are significantly lower than those in the 40° C. group at each time point after soaking. Therefore, the soaking temperature is selected as 40° C.

3) Investigation on the Amount of Ethanol

It was found in a preliminary test that, the fresh body of *Periplaneta americana* L. can be soaked just in 1.5 BV ethanol. Therefore, 1.5 BV, 2.5 BV and 3.5 BV 25% ethanol were added for comparison test.

Fresh body of *Periplaneta americana* L. was weighed by 100 g/portion, placed in a glass bottle, added with 150 ml, 250 ml, and 350 ml of 25% ethanol respectively, sealed, and left to stand for 10 days at 40° C. The soaked samples were taken out, reflux extracted with 70% ethanol for three times, in which 250 ml of ethanol was added for the first extraction, and 300 ml of ethanol was added for the second and third times, and each extraction was performed for 1 h, and filtered. The filtrates were combined. The extract was cooled down, mixed evenly, and filtered. The contents of free amino acids and water-soluble total solids were determined in the filtrate. The results are shown in table 9.

TABLE 9

Results of investigation on soaking by different BVs of ethanol (n = 2)

| Evaluation indexes | 1.5 BV | 2.5 BV | 3.5 BV |
|---|---|---|---|
| Total solids (g) | 15.50 | 14.58 | 14.54 |
| Free amino acids (g) | 5.12 | 4.49 | 4.01 |

According to the results in Table 9, a column diagram is plotted, in which the addition amount of 25% ethanol is the horizontal ordinate, and the total solids and free amino acids is the longitudinal ordinate, as shown in FIG. 9.

The above test results show that the addition amount of 25% ethanol has little effect on total solids and free amino acids, in which it is slightly higher at the amount of 1.5 BY. It may lie in that the water content in the fresh body of *Periplaneta americana* L. is 50% or above, resulting in a slight decrease in the concentration of ethanol, and the degree of decrease is inversely proportional to the addition amount of ethanol. The experimental results are consistent with the previous results that the soaking concentration of ethanol is inversely proportional to the yield of water-soluble total solids and free amino acids. Therefore, the addition amount of 25% ethanol is 1.5 BV.

4) Further Investigation on the Soaking Temperature and Soaking Time

Fresh body of *Periplaneta americana* L. was weighed by 100 g/portion, placed in a glass bottle, added with 150 ml of 25% ethanol respectively, sealed, and left to stand for 60 days at 20° C., 30° C., 40° C., 50° C. and 60° C., respectively. The soaked samples were taken out every 10 days, reflux extracted with 70% ethanol for three times, in which 250 ml of ethanol was added for the first extraction, and 300 ml of ethanol was added for the second and third times, and each extraction was performed for 1 h, and filtered. The filtrates were combined. Ethanol was recovered under reduced pressure at 65° C. until there was no smell of ethanol. The extract was cooled down, added with water to 500 ml, mixed evenly, and centrifuged (at 12000 r/min) for 30 min to obtain a supernatant. The supernatant was filtered, and the contents of free amino acids and water-soluble total solids were determined in the filtrate. The results are shown in Table 10.

change after 40 days. Therefore, the soaking time for the fresh body of *Periplaneta americana* L. is determined as 20-40 days.

5) Comparative Study on Extracts of Three Species of *Periplaneta americana* L.

Preliminary tests showed that, the contents of total amino acids, free amino acids, peptides and water-soluble total

TABLE 10

| Temperature | Indexes | Day 0 | Day 10 | Day 20 | Day 30 | Day 40 | Day 50 | Day 60 |
|---|---|---|---|---|---|---|---|---|
| 20° C. | Amino acids | 0.27 | 2.66 | 4.12 | 5.30 | 5.91 | 6.14 | 6.23 |
| | Total solids | 3.19 | 7.07 | 9.93 | 10.64 | 11.28 | 11.45 | 11.56 |
| 30° C. | Amino acids | 0.27 | 3.31 | 4.97 | 6.25 | 6.78 | 7.09 | 7.13 |
| | Total solids | 3.19 | 8.24 | 11.95 | 13.21 | 13.66 | 13.77 | 13.85 |
| 40° C. | Amino acids | 0.27 | 4.49 | 6.41 | 7.58 | 8.27 | 8.52 | 8.73 |
| | Total solids | 3.19 | 11.62 | 15.73 | 16.45 | 17.32 | 17.41 | 17.58 |
| 50° C. | Amino acids | 0.27 | 2.18 | 3.26 | 4.25 | 5.13 | 5.42 | 5.51 |
| | Total solids | 3.19 | 6.66 | 9.04 | 10.05 | 10.73 | 10.81 | 10.87 |
| 60° C. | Amino acids | 0.27 | 1.52 | 2.36 | 2.60 | 2.81 | 2.94 | 3.11 |
| | Total solids | 3.19 | 6.37 | 8.15 | 8.56 | 8.83 | 8.99 | 9.08 |

Changes the yields of total free amino acids and water soluble (n = 2)

According to the results in Table 10, a change trend diagram is plotted, in which the soaking time is the horizontal ordinate and the yield of free amino acids and water-soluble total solids is the longitudinal ordinate, as shown in FIG. 10 and FIG. 11.

It can be seen from the test results that the soaking temperature has a great influence on the yield of total free amino acids and water-soluble total solids. The total free amino acids and water-soluble total solids in the 40° C. group are the highest at each time point after soaking. Considering the production cost and actual situation, it is more appropriate to control the soaking temperature at 40° C. (±2° C.).

Meanwhile, the yield of the free amino acids and water-soluble total solids shows a rapid increase in the first 20 days, a relatively slow increase thereafter, and no significant solids in the alcohol extract of the fresh body of *Periplaneta americana* L. soaked in 25% ethanol increased significantly. The following is a test for comparing relative substances in the extracts prepared from fresh body of *Periplaneta americana* L (MLX), dried body of *Periplaneta americana* L. (MLG), and fresh body of after soaking in 25% ethanol (MLP) according to the same preparation processes, and in vitro inhibition to inflammation thereof.

① Preparation Processes of MLX, MLG and MLP Extracts

The same batch of fresh body of *Periplaneta americana* L. is weighed by 1000 g/portion, and prepared into three kinds of extracts of *Periplaneta americana* L. having the same model and specification according to the preparation process of MLX, MLG and MLP, as show in Table 11 for details.

TABLE 11 preparation process of MLX, MLG and MLP (n = 1)

| Sample name | MLX | MLG | MLP | Note |
|---|---|---|---|---|
| Batch number of fresh body | 190401 | 190401 | 190401 | The same batch of fresh body of *Periplaneta americana* L. |
| Weight of fresh body | 1000 g | 1000 g | 1000 g | Having the same weight |
| Pre-treatment | / | Dried at 60° C. (449 g after drying) | Standing at 40° C. for 20 days in 1.5 L 25% ethanol | Subjected to three different pretreatment processes |
| Preparation process | reflux extracted in 70% ethanol for three times, in which each extraction was performed for 1 h, and 4 L (being supplemented to 4 L for MLP group), 3 L, and 3 L of ethanol was added for each extraction; recovering ethanol from the solution at 60° C. under reduced pressure until there is no smell of ethanol, | | | Subjected to the same preparation process |

TABLE 11-continued

| preparation process of MLX, MLG and MLP (n = 1) | | | |
|---|---|---|---|
| Sample name | MLX | MLG | MLP | Note |
| | adding water to 10 L, boiling for 1 h, standing overnight, filtering, and subjecting the filtrate to concentrating at 70° C. under reduced pressure; and adding water to the concentrated solution to 450 ml, mixing evenly, bottling by 10 ml/bottle, and sterilizing at 105° C. for 45 min, and obtained. | | | |
| Sample volume | 450 ml | 450 ml | 450 ml | Diluted to the same volume |
| Sample specification | 1 g/ml | 1 g/ml | 1 g/ml | Having the same model and specification, based on dried body |
| Sample package | 10 ml/bottle | 10 ml/bottle | 10 ml/bottle | Having the same package |
| Sample batch No. | 190501 | 190502 | 190601 | / |

② Comparison of Relative Substances in MLX, MLG and MLP Extracts

The contents of total solids, nucleoside bases, free amino acids, total amino acids and peptides were determined in MLX, MLG and MLP. The results are shown in Table 12.

TABLE 12

| Determination results of various substances in samples | | | | |
|---|---|---|---|---|
| Sample No. | Total solids (g) | nucleoside bases (g) | free amino acids (g) | total amino acids (g) | Peptides (g) |
| MLP | 127.8 | 0.6 | 58.5 | 81.5 | 23.0 |
| MLG | 50.7 | 0.6 | 11.7 | 23.5 | 11.8 |
| MLX | 31.1 | 0.5 | 4.7 | 12.0 | 7.3 |

Note:
1. Nucleoside bases include uracil, hypoxanthine, xanthine and inosine.
2. Peptides = total amino acids – free amino acids.
3. The results of various substances are the total amount thereof in 1000 g fresh body.

According to the results in Table 12, a column chart is plotted, in which various substances in the extract are the horizontal ordinate and the total amount is the longitudinal ordinate. The results are shown in FIG. 12.

According to the results in Table 12, the amount of total free amino acids, peptides and nucleoside bases in total solids are calculated. The results are shown in FIG. 13.

TABLE 13

| Content of various substances in total solids in the sample | | | |
|---|---|---|---|
| Sample No. | Total free amino acids (%) | Peptides (%) | nucleoside bases (%) | Others (%) |
| MLP | 45.8 | 18.0 | 0.5 | 35.8 |
| MLG | 23.1 | 23.3 | 1.2 | 52.5 |
| MLX | 15.1 | 23.5 | 1.6 | 59.8 |

According to the results in table 13, the pie chart of various substances in MLP, MLG and MLX samples in total solids is plotted, as shown in FIG. 13.

The results showed that, except for nucleoside bases, other substances in the soaked group of fresh body of *Periplaneta americana* L. are significantly higher than those in the fresh body group and the dried group, in which the amount of water-soluble total solids was 4 times higher than those in the fresh body group and was 2 times higher than those in the dried body group; the amount of free amino acids was 10 times higher that in the fresh body group and 5 times or higher than that in the dried group; the amount of total amino acids was 7 times or higher than that in the fresh body group and 3 times or higher than that in the dried body group; and the amount of peptides was 3 times or higher that in the fresh body group and 2 times or higher that in the dried body group.

Although the extracts of the fresh body group, dried body group and soaked fresh body group contain free amino acids, peptides, nucleoside bases and other substances, the proportions and contents of various components are significantly different, indicating that there is a significantly different material basis among MLX, MLG and MLP extracts.

③ Results of Comparative Study on Anti-Inflammatory Effect In Vitro

Based on TNF-a-IL-6/iNOS-NO inflammatory signal pathway, the regulatory effects of drugs MLG, MLP and MLX on LPS induced inflammation of mouse macrophages (RAW264.7) were evaluated.

The original solution of drugs MLG, MLP and MLX was diluted by 80 times, 120 times and 160 times, respectively, incubated with cells for 12 h in advance, and used to stimulate cells to induce inflammation by a final concentration of 1 μg/ml LPS. Enzyme linked immunosorbent assay (ELISA) and Griess method were used to detect the release amount of TNF-α at 50 min, and IL-6 at 4 h and NO at 12 h upon LPS stimulation.

The results showed that the effect of inhibition to the release of LPS induced TNF-α by MLG, MLP and MLX is not obvious. However, MLG, MLP and MLX diluted by different dilution ratios can significantly inhibit the release of NO and IL-6 induced by LPS, in which MLP has the most significant inhibitory effect on NO and IL-6 under the same dilution ratio. (see Annex 1 for details: Study on the effects of MLG, MLP and MLX on LPS stimulated mouse macrophage inflammation model)

In conclusion, the contents of water-soluble total solids, total free amino acids, total amino acids and peptides in the extract made from the fresh body of *Periplaneta americana* L. by the same process, that is, soaking in 25% ethanol for 20-40 days, are significantly higher than those in the extracts made from fresh body/dried body of *Periplaneta americana* L., and the extract from soaked fresh body has the highest regulatory effect on LPS induced mouse macrophage (RAW264.7) inflammation.

④ MLG, MLP and MLX Cell Test Results

The original solution of drugs MLG, MLP and MLX was diluted by 80 times, 120 times and 160 times respectively, incubated with cells for 12 hours in advance, and then added with 1 μg/mL LPS to stimulate cell inflammation. Enzyme linked immunosorbent assay (ELISA) and Griess method were used to detect the release amount of TNF-α at 50 min, IL-6 at 4 h, NO at 12 h upon LPS stimulation, and the regulatory effects of drugs MLG, MLP and MLX on LPS induced cellular inflammation were investigated.

The cells in logarithmic growth stage were inoculated into 24 well plates to provide a cell density of $6\times10^5$/ml and 500 μL per well. After incubation for 12 hours, the culture medium was discarded and 500 μL DMEM high glucose medium was added to the blank and model groups, and 500 mL culture medium having drug solutions of different con-absorbance value of the sample at the lower limit of the standard curve, it is counted as lower than the relevant value, and the relevant statistics are calculated as 0 mean and 0 variance.

The samples were detected according to the above methods and time points, the results showed that, compared with the model group, MLG, MLP and MLX had no inhibitory effect on TNF-α. Various drugs had significant inhibitory effects on the production of IL-6 (P<0.05) in a dose-dependent manner. Among them, MLP had the highest effect, and the inhibitory effect of MLG on IL-6 decreased with the increase of dose. MLG, MLP and MLX had significant inhibitory effects on the release of NO (P<0.05) in a dose-dependent manner, and, among them, MLP had the highest effect. The results are shown in following FIG. 14 and Table 14.

TABLE 14

| | | Effects of drugs on cytokines (n = 3) | | |
|---|---|---|---|---|
| | | | Detected Indexes | |
| Drugs | | NO (μM) | IL-6(pg/mL) | TNF-α(pg/mL) |
| Con | | 0.33 ± 0.14 | 20.1 ± 2.45 | 100.81 ± 4 |
| model | | 19.92 ± 1.13* | 870.95 ± 90.6* | 2161.68 ± 276.75*# |
| Andro. | | 1.86 ± 0.34*# | 286.07 ± 47.81*# | 592.26 ± 45.7*# |
| MLG | L | 13.15 ± 0.5*# | 177.02 ± 10.55*# | 8533.16 ± 300.82*# |
| | M | 10.21 ± 1.15*# | 305.11 ± 8.86*# | 8762.95 ± 188.99*# |
| | H | 8.32 ± 0.3*# | 586.83 ± 26.62*# | 9278.1 ± 353.58*# |
| MLP | L | 1.06 ± 0.49* | 54.65 ± 2.16# | 6880.76 ± 127.49*# |
| | M | 0.1 ± 0.03# | 50.67 ± 2.44# | 7530.86 ± 232.5*# |
| | H | 1.01 ± 0.69# | 55.87 ± 3.11# | 8167.12 ± 212.48*# |
| MLX | L | 10.94 ± 11.06*# | 223.18 ± 18.2*# | 4042.71 ± 225.24*# |
| | M | 8.93 ± 8.33*# | 144.73 ± 28.34*# | 4288.13 ± 43.36*# |
| | H | 7.34 ± 6.79*# | 134.52 ± 13.03*# | 5240.74 ± 268.73*# |

Note:

compared with Con group,

*P < 0.05; and compared with model group,

P < 0.05 centrations was contained in the drug administration group (the solvent content in individual groups were identical). They were cultured in a 37° C. and 5% $CO_2$ cell incubator for another 12 h, and 20 μL of supernatant was removed from each individual wells. 20 μL DMEM medium was added to the blank group, and 20 μL medium containing 0.025 μg/mL LPS was added to the other groups, so that LPS had a final concentration of 1 μg/mL. After incubating another 50 min, 300 μL supernatant was suctioned from each individual wells, and filled into a 0.6 mL EP tube for TNF-α detection.

The same operation was performed for parallel plates. After adding LPS, incubation was performed for 4 h, and 300 μL supernatant was suctioned from each individual wells, and filled into a 0.6 mL EP tube for IL-6 detection.

The same operation was performed for parallel plates. After adding LPS, incubation was performed for 12 h, and 300 μL supernatant was suctioned from each individual wells, and filled into a 0.6 mL EP tube for NO detection.

All indexes were tested strictly in accordance with the instructions of kits. Finally, the absorbance value at the specific wavelengths were detected on an enzyme labeling instrument, and the content of indexes of each sample were calculated according to the standard curve prepared by the same method. If the absorbance value is lower than the ⑤ Effects of Three Extracts of MLX, MLG and MLP on Increase of Skin Capillary Permeability Induced by Xylene in Mice.

Fifty mice weighing 18-22 g were randomly divided into five groups according to their body weights: MLX, MLG and MLP test groups. 0.2 mg/kg dexamethasone was used as the positive control drug, and the model control group was perfused with NS of equal volume. various groups were administered once a day for seven times. One hour after the last administration, various mice were injected with 0.5% Evans blue normal saline solution by 0.1 ml/10 g bw via caudal vein, and then xylene were dropped by 30 μL/per mouse on the abdominal skin depilated 24 hours in advance. After 20 minutes, the mice were killed by removing the cervical vertebra. The blue stained skin on the abdomen was cut off, and cut into pieces with surgical scissors, placed into a test tube with a plug, added with and soaked in 5 ml of acetone normal saline (7:3), placed in the dark for 72 hours, and centrifuged at 3000 r/min for 10 minutes to obtain a supernatant. Colorimetric detection was performed at the wavelength of 590 nm on a spectral scanning multifunctional reader to measure the absorbance (OD value). The permeability is represented by OD value, and the results are statistically compared. The results are shown in table 15.

TABLE 15

| Groups | Number of mice (n) | Dosage (mL/kg) | Administration number (times) | OD value | Inhibitory rate (%) |
|---|---|---|---|---|---|
| Model group | 10 | 10 | 7 | 0.476 ± 0.058 | / |
| dexamethasone | 10 | 0.375 mg/kg | 7 | 0.092 ± 0.017** | 80.7% |
| MLP | 10 | 2 | 7 | 0.160 ± 0.017** | 66.4% |
| MLG | 10 | 2 | 7 | 0.272 ± 0.022**$^{\#\#}$ | 42.9% |
| MLX | 10 | 2 | 7 | 0.343 ± 0.062**$^{\#\#}$ | 27.9% |

Effects of three extracts on the increase of skin capillary permeability induced by xylene in mice ($\bar{x} \pm s$)

Note:
*P < 0.05,
**P < 0.01 compared with model group;
$^{\#}$P < 0.05,
$^{\#\#}$P < 0.01 compared with MLP group The results show that, after xylene modeling, the skin capillary permeability of mice increased significantly and the degree of skin blue staining increased. Dexamethasone administration could inhibit the increase of skin capillary permeability caused by xylene, and the degree of skin blue staining was significantly lower than that of the model group (P<0.01), with a inhibition rate of more than 80%. After intragastric administration of MLX, MLG and MLP extracts, the degree of skin blue staining in various extract groups was also significantly reduced compared with the model group (P<0.05 or P<0.01), in which the MLP group was the most significantly reduced, and there was a significant difference with MLX group and MLG group.

⑥ Effects of Three Extracts of MLX, MLG and MLP on Cotton Ball Granuloma in Mice Fifty mice weighing 18-22 g were taken, 10/group, half male and half female. The mice were fixed, and disinfected on the chest with iodine. Iodine was removed with 75% alcohol cotton ball. A small hole was cut in the chest, 20 mg high-pressure sterilized cotton ball was implanted into the armpit subcutaneously from the incision with ophthalmic forceps, and then the skin was sutured. Starting from the day of operation, the administration group was given MLX, MLG and MLP extracts (2 ml/kg) and dexamethasone (0.2 mg/kg), and the model control group was given NS of equal volume. The above groups were administrated for 7 consecutive days. Before the end of the test on the 8th day, the body weight was measured, then the mice were killed by taking off the cervical vertebra. The implanted cotton ball was taken out together with the surrounding connective tissue, removed of the adipose tissue, wet weighted, placed into the oven at 60° C. for 24 hours, and weighed on a precision balance. The weight of granuloma was obtained by subtracting the original weight of cotton ball from the weighed weight, and the comparison and statistical analysis between groups were carried out. The results are shown in Table 16.

TABLE 16

| Groups | Number of mice (n) | Dosage (mL/kg) | Administration number (times) | Wet weigh of granuloma (mg) | Dry weigh of granuloma (mg) |
|---|---|---|---|---|---|
| Model group | 10 | 10 | 7 | 421.4 ± 53.67 | 65.38 ± 9.34 |
| Dexamethasone | 10 | 0.2 mg/kg | 7 | 252.3 ± 33.6** | 35.63 ± 8.38** |
| MLP | 10 | 2 | 7 | 261.2 ± 35.49** | 37.29 ± 7.7** |
| MLG | 10 | 2 | 7 | 364.6 ± 37.86**$^{\#\#}$ | 50.83 ± 8.87**$^{\#\#}$ |
| MLX | 10 | 2 | 7 | 395.8 ± 34.92$^{\#\#}$ | 55.68 ± 7.79*$^{\#\#}$ |

Effects of three extracts on cotton ball granuloma in mice ($\bar{x} \pm s$)

Note:
*P < 0.05,
**P < 0.01 compared with model group;
$^{\#}$P < 0.05,
$^{\#\#}$P < 0.01 compared with MLP group The results show that, dexamethasone administration significantly inhibited the formation of cotton ball granuloma, and the wet and dry weight of granuloma were significantly reduced than those in the model group (P<0.01). Compared with the model group, the wet weight and dry weight of MLG and MLP granuloma were also significantly reduced (P<0.05 or P<0.01), especially in MLP group, which was significantly different from MLX group and MLG group.

In conclusion, cell test and animal test show that three extracts of MLX, MLG and MLP have the effect of inhibiting inflammation, among which MLP has the highest effect.

Experimental Example 2 Investigation on Extraction Conditions

Fresh body of *Periplaneta americana* L. was weighed by 100 g/portion, placed in a glass bottle, added with 150 ml of 25% ethanol respectively, sealed, left to stand for 20 days at 40° C., taken out, reflux extracted with 50%, 60%, 70% and 80% ethanol for three times, in which 2.5 BV (250 ml) of ethanol was added for the first extraction, and 3 BV (300 ml) of ethanol was added for the second and third times, and each extraction was performed for 1 h, and filtered through 10 mesh filtering net. The filtrates were combined, cooled down, and filtered via filter paper, and obtained. The amount and extraction ratio of total free amino acids were detected in the obtained filtrate. The results are shown in FIG. 17.

TABLE 17

| Results of investigation on extraction solvent (n = 2) | | | | | |
|---|---|---|---|---|---|
| Concentration of ethanol (%) | 50 | 60 | 70 | 80 | RSD % |
| Extraction ratio (%) | 18.25 | 18.18 | 16.48 | 16.26 | 6.2 |
| Amount of total free amino acids (g) | 7.02 | 6.61 | 6.30 | 6.64 | 4.5 |
| Filtering time (min) | 3 | 2 | 1 | 1 | / |
| State of extracted solution | Turbid | Turbid | Relatively clear | Clear | / |

The results show that, the concentration of ethanol has little effect on the extraction amount and the extraction ratio of total free amino acids. The extract ratio of 80% ethanol group is slightly lower, but the clarity is the highest and the filtration speed is the fastest, which was convenient for production and operation. At the same time, there are few kinds of macromolecular proteins in the 80% ethanol extract, which is convenient for the subsequent purification process. Therefore, 80% ethanol is selected as the extraction solvent.

2) Selection of Particle Size

The fresh body of *Periplaneta americana* L. soaked in ethanol has soft texture, and tends to form homogenate if pulverized, resulting in difficulty in filtering the extract. Moreover, the fresh body of *Periplaneta americana* L. has 2.5-3.2 cm length, 1-1.4 cm width, and only about 1.3 g weight, that is, small size. Therefore, direct feeding of the whole body will not affect the extraction effect.

3) Orthogonal Extraction Test

There are many factors affecting the ethanol extraction effect of the fresh body of *Periplaneta americana* L. after soaking. Through the analysis of the physical and chemical properties of the substances as contained, it is decided to take the times of extraction, extraction time and 80% ethanol addition as the investigation factors. Combined with actual production, three levels are designed for each factor. The test scheme is shown in Table 18.

TABLE 18

| Factor level table | | | |
|---|---|---|---|
| | Factors | | |
| | times of extraction (times) | Extraction time (h) | Adding amount (times) |
| Level | A | B | C |
| 1 | 1 | 1 | 3 |
| 2 | 2 | 1.5 | 4 |
| 3 | 3 | 2 | 5 |

According to the factor level table, L9 ($3^4$) orthogonal table is selected for the test. At most four three-level factors can be arranged according to this table. In this experiment, there are only three factors randomly arranged in the table, and the fourth column is empty. By filling the factors of the test items into the table from left to right, test results are filled into Table 19, in which the extraction amount and the extraction ratio of total free amino acids are used as evaluation indexes, and variance analysis is performed on the test results.

TABLE 19

| | Results of orthogonal test (n = 2) | | | | | |
|---|---|---|---|---|---|---|
| | Factors | | | | | |
| Groups | Extraction times A | Extraction time B | solids/liquid ratio C | Control D | Extraction amount a | total free amino acids b |
| 1 | 1 | 1 | 1 | 1 | 12.55 | 5.73 |
| 2 | 1 | 2 | 2 | 2 | 12.85 | 5.73 |
| 3 | 1 | 3 | 3 | 3 | 14.17 | 6.14 |
| 4 | 2 | 1 | 2 | 3 | 16.40 | 6.98 |
| 5 | 2 | 2 | 3 | 1 | 16.08 | 6.80 |
| 6 | 2 | 3 | 1 | 2 | 15.11 | 6.56 |
| 7 | 3 | 1 | 3 | 2 | 16.71 | 6.75 |
| 8 | 3 | 2 | 1 | 3 | 16.39 | 7.18 |
| 9 | 3 | 3 | 2 | 1 | 17.07 | 6.94 |
| Ka1 | 13.19 | 15.22 | 14.68 | 15.23 | | |
| Ka2 | 15.86 | 15.11 | 15.44 | 14.89 | | |
| Ka3 | 16.72 | 15.45 | 15.65 | 16.65 | | |
| Ra | 3.53 | 0.34 | 0.97 | 1.76 | | |
| Kb1 | 5.87 | 6.49 | 6.49 | 6.49 | | |
| Kb2 | 6.78 | 6.57 | 6.550 | 6.35 | | |
| Kb3 | 6.96 | 6.55 | 6.56 | 6.77 | | |
| Rb | 1.09 | 0.08 | 0.07 | 0.42 | | |

According to variance analysis of the test results, it is found that clinical Fp table of F Test is $F_{0.05}(2,2)=19.0$ and $F_{0.01}(2,2)=99.0$. The results are shown in Table. 20.

TABLE 20

| | Results of variance analysis | | | | |
|---|---|---|---|---|---|
| Source of variation | Dependent variable | Sum of squares of deviations | Freedom | F value | Significance |
| A | Extraction amount | 20.37 | 2 | 23.23 | * |
| | Amino acids | 2.05 | 2 | 7.51 | |
| B | Extraction amount | 0.18 | 2 | 0.21 | |
| | Amino acids | 0.01 | 2 | 0.04 | |

TABLE 20-continued

| | | Results of variance analysis | | | |
|---|---|---|---|---|---|
| Source of variation | Dependent variable | Sum of squares of deviations | Freedom | F value | Significance |
| C | Extraction amount | 1.56 | 2 | 1.78 | |
| | Amino acids | 0.01 | 2 | 0.03 | |
| Error e | Extraction amount | 0.88 | 2 | | |
| | Amino acids | 0.27 | 2 | | |

The results of range analysis show that, the extraction time and solid-liquid ratio had little effect on the extraction amount and extraction ratio of free amino acids, and the extraction times had a great effect on the extraction amount and extraction ratio of free amino acids. At the same time, the results of variance analysis also shows that the extraction times has a large F value, and has a significant effect on the extraction amount. The two factors, that is, extraction time and solid-liquid ratio, have no significant impact on the extraction results.

To sum up, considering the improvement of production efficiency and reduction of production cost, the best extraction process is determined as follows: $A_3B_1C_1$, that is, performing reflux extraction by 80% ethanol for three times, in which 1.5 BV (supplemented to 3 BV) was added for the first time, 3 BV were added for the second and third times, and extraction was performed for 1 h each time.

4) Test According to a Preferred Process ($A_3B_1C_1$)

According to the optimum technological conditions determined by orthogonal test, the yield of total free amino acids and extraction ratio were investigated.

Fresh body of *Periplaneta americana* L. was weighed by 1000 g/portion, placed in a glass bottle, added with 1.5 L of 25% ethanol respectively, sealed, left to stand for 20 days at 40° C., taken out, reflux extracted with 80% ethanol for three times, in which 1.5 L of ethanol was added for the first extraction, and 3.0 L of ethanol was added for the second and third times, and each extraction was performed for 1 h, and filtered. The filtrates were combined, cooled down, and filtered. The filtrates were taken and detected the amount of total free amino acids and extraction ratio. The results are shown in Table 21.

TABLE 21

| Result of process verification (n = 2) | |
|---|---|
| Yield of total free amino acids (%) | Extraction ratio (%) |
| 6.41 | 16.31 |

The results show that, after soaking, the fresh body of *Periplaneta americana* L. was extracted with 80% ethanol for three times, in which each extraction was performed for 1 h, and 3 BV of ethanol was added for extraction. The yield of total free amino acids was 6.41% and the extraction ratio was 16.31%.

Experimental example 3 Investigation on the preparation process of mixture of ethanol extracts of the fresh body of *Periplaneta americana* L.

1) Preparation of *Extractum* for Clarification Process and Preparation of Clarifying Agent ① Preparation of Dilute *Extractum* for Clarification Process Fresh body of *Periplaneta americana* L. was weighed by 1000 g/portion, placed in a glass bottle, added with 1500 ml of 25% ethanol, sealed, left to stand for 20 days at 40° C., taken out, reflux extracted with 80% ethanol for three times, in which each extraction was performed for 1 h, 1.5 BV of ethanol (supplemented to 3.0 BV, 1.5 L) was added for the first extraction, and 3.0 BV (3.0 L) of ethanol was added for the second and third extractions, and filtered. Ethanol was recovered from the filtrate at 60-90° C. under reduced pressure, and the filtrate was concentrated to a relative density of 1.04-1.08 (60° C.), added with suitable amount of water to prepare a thin *extractum* of 1.0 g crude drug/ml, and refrigerated, being ready for use.

② Preparation of Clarifying Agent

1% gelatin solution: 10 g gelatin was weighed, soaked in 500 ml purified water for 30 min, then added with 500 ml hot water (>95° C.) under stirring until all gelatin was completely dissolved, and cooled down, and obtained.

1% chitosan solution: 10 g of chitosan was weighed, added with 1000 ml of 1% glacial acetic acid solution under stirring, and left to stand until it was completely dissolved, and obtained.

Chitosan: gelatin (1:3): 1% chitosan solution and 1% gelatin solution was mixed evenly by the ratio of 1:3.

2) Selection of Clarifying Agent 8 portions of the above-mentioned thin *extractum*, 30 ml/part (equivalent to 30 g crude drug), was taken, added with 180 ml purified water (i.e. crude drug:drug solution=1: 7) respectively, well mixed, added with 30 ml purified water, 30 ml 1% gelatin solution, 30 ml 1% chitosan solution and 30 ml mixed solution of chitosan/gelatin (1:3) at 60° C. under stirring, stirred at 60° C. for another 10 min, cooled, and refrigerated overnight. The extracts were taken out, and filtered. The filtration time of the samples was recorded, the condition of the filtrate was observed, and the content and light transmittance of total solids and total free amino acids of the filtrate were detected. The results are shown in table 22.

TABLE 22

| Selection results of clarifying agent (n = 2) | | | | | | |
|---|---|---|---|---|---|---|
| Kinds of clarifying agents | Added amount (ml) | Filtering time (min) | Clarification | Yield of total solids (%) | Yield of total free amino acids (%) | Transmittance (%) |
| Purified water | / | 57 | * | 14.57 | 6.60 | 9.72 |
| 1% gelatin solution | 30 | >120 | * | 14.86 | 6.37 | 23.71 |
| 1% chitosan solution | 30 | 33 | * | 16.30 | 6.25 | 31.41 |
| chitosan/gelatin 1:3 | 30 | 5 | *** | 15.04 | 6.33 | 83.19 |
| RSD (%) | / | / | / | 5.1 | 2.4 | / |

Note:
1 The clarification effect is expressed by clarification (*), relatively clarification (), turbidity (*); and
2. The suction bottle, Buchner funnel and filter materials used for filtering each group of samples are of the same model and specification.

It can be seen from the test results that, there is no significant difference in the yield of total solids and total free amino acids among the four groups. Chitosan/gelatin (1:3) provides the best clarification effect, the shortest filtration time, clear filtrate and the highest transmittance of filtrate. Therefore, chitosan/gelatin is selected as the clarifying agent for the study of clarification process.

3) Selection of Clarifying Proportion 10 portions of the thin *extractum* was weighed, 30 ml/part (equivalent to 30 g crude drug), added with 180 ml purified water (i.e. crude drug:drug solution=1:7), well mixed, added with 30 ml of chitosan/gelatin (2:1), chitosan/gelatin (1:1), chitosan/gelatin (1:2), chitosan/gelatin (1:3) and chitosan/gelatin (1:4) respectively at 60° C. under stirring, all clarifying agents are 1% mixture solutions, stirred at 60° C. for another 10 min, cooled, and refrigerated overnight. The extracts were taken out and filtered. The filtration time of the samples was recorded, the condition of the filtrate was observed, and the content and light transmittance of total solids and total free amino acids of the filtrate were detected. The results are shown in table 23.

TABLE 23

| | | | | Yield of | |
| | | | Yield of | total | Transmit- |
| Ratios of | Filtering | | total | amino | tance |
| clarifying | time | Conditions of | solids | acids | rate |
| agents | (min) | Clarification | (%) | (%) | (%) |
|---|---|---|---|---|---|
| 2:1 | >66 | * | 14.63 | 6.21 | 55.53 |
| 1:1 | 53 | *** | 15.15 | 6.58 | 82.66 |
| 1:2 | 14 | *** | 14.58 | 6.56 | 87.80 |
| 1:3 | 3 | *** | 14.56 | 6.51 | 88.32 |
| 1:4 | 3 | *** | 14.75 | 6.60 | 86.03 |

Note:
1 The clarification effect is expressed by clarification (*), relatively clarification (), turbidity (*); and
2. The suction bottle, Buchner funnel and filter materials used for filtering each group of samples are of the same model and specification.

It can be seen from the test results that, the change in the ratio of chitosan/gelatin has no significant difference in the yield of total solids and total free amino acids. Chitosan/gelatin by a ratio of (1:3) and (1:4) provide the shortest filtration time and the best clarification effect. Chitosan/gelatin by a ratio of (1:3) provides the highest transmittance for filtrate. Therefore, the ratio of chitosan/gelatin is selected as (1:3).

4) Investigation on the Amount of Water Added 12 portions of thin *extractum* were weighed, added with an appropriate amount of water to prepare solutions with crude drug concentrations of 1 g/ml, 1/3 g/ml, 1/5 g/ml, 1/7 g/ml, 1/9 g/ml and 1/11 g/ml respectively, slowly added with a clarifying agent at 60° C., stirred for 10 min, cooled, and refrigerated overnight. The extracts were taken out and filtered. The filtration time of the samples was recorded, the Clarification condition of the filtrate was observed, and the content and light transmittance rate of total solids and total free amino acids of the filtrate were detected. The results are shown in table 24.

TABLE 24

Investigation results of water added (n = 2)

| | | | | Yield of | |
| | | | | total | |
| Ratio of | | | Yield of | free | |
| Crude | Filtering | | total | amino | Transmittance |
| drug/drug | time | Condition of | solids | acids | rate |
| solution | (min) | Clarification | (%) | (%) | (%) |
|---|---|---|---|---|---|
| 1:1 | >33 | * | 13.87 | 6.35 | 2.80 |
| 1:3 | 1 | *** | 14.41 | 6.13 | 86.56 |

TABLE 24-continued

Investigation results of water added (n = 2)

| | | | | Yield of | |
| | | | | total | |
| Ratio of | | | Yield of | free | |
| Crude | Filtering | | total | amino | Transmittance |
| drug/drug | time | Condition of | solids | acids | rate |
| solution | (min) | Clarification | (%) | (%) | (%) |
|---|---|---|---|---|---|
| 1:5 | 1 | *** | 14.17 | 6.24 | 88.42 |
| 1:7 | 3 | *** | 14.30 | 6.24 | 88.76 |
| 1:9 | 4 | *** | 14.49 | 5.15 | 88.93 |
| 1:11 | 4 | *** | 14.62 | 5.33 | 84.17 |

Note:
1 The clarification effect is expressed by clarification (*), relatively clarification (), turbidity (*); and
2. The suction bottle, Buchner funnel and filter materials used for filtering each group of samples are of the same model and specification.

It can be seen from the test results that, change of crude drug concentration between 1/3-1/7 g/ml has no significant effect on the yield of total free amino acids and total solids. The crude drug concentration of lower than 1/3 g/ml provides a better clarification effect, faster filtration speed, and a light transmittance rate of the filtrate of more than 80%, achieving a balance between production efficiency and cost. Therefore, the crude drug concentration is selected as 1/3 g/ml.

5) Investigation on Amount of Clarifying Agent 12 portions of dilute extracts were weighed, added with water to prepare solutions with crude drug concentrations of 1/3 g/ml respectively, well mixed, slowly added with a clarifying agent with 0.1~1.2 ml/g crude drug at 60° C., stirred for 10 min, cooled, and refrigerated overnight. The extracts were taken out and filtered. The filtration time of the samples was recorded, the clarification condition of the filtrate was observed, and the content and light transmittance rate of total solids and total free amino acids of the filtrate were detected. The results are shown in table 25.

TABLE 25

Investigation results of the amount of clarifying agent (n = 2)

| | | | | Yield of | |
| amount of | | | | total | |
| clarifying | | | Yield of | free | Transmit- |
| agent | Filtering | | total | amino | tance |
| (ml/g crude | time | conditions of | solids | acids | rate |
| drug) | (min) | Clarification | (%) | (%) | (%) |
|---|---|---|---|---|---|
| 1.2 | 16 | ** | / | / | 69.20 |
| 1.0 | 2 | *** | 15.29 | 6.02 | 84.61 |
| 0.8 | 1 | *** | 15.32 | 5.92 | 88.76 |
| 0.6 | 1 | *** | 15.65 | 6.39 | 87.67 |
| 0.4 | 1 | *** | 15.72 | 6.47 | 76.31 |
| 0.2 | 1 | *** | 16.09 | 6.42 | 73.97 |
| 0.1 | 1 | ** | 17.06 | 6.40 | 65.21 |

Note:
1 The clarification effect is expressed by clarification (*), relatively clarification (), turbidity (*); and
2. The suction bottle, Buchner funnel and filter materials used for filtering each group of samples are of the same model and specification.

The results showed that, when the amount of clarifying agent is 0.2-1.0 ml/g crude drug, the filtrate is clarified, the filtration time is short, and the light transmittance rate is more than 70%. When the amount is 0.2-0.6 ml/g crude drug, the yield of total solid and total free amino acids in the clarifying agent is all higher. Therefore, the amount of clarifying agent is 0.2-0.6 ml/g crude drug.

6) Investigation of Clarifying Temperature 8 portions of thin *extractum* were weighed, added with water to prepare solutions with crude drug concentrations of ⅓ g/ml respectively, well mixed, slowly added with a clarifying agent of 0.6 ml/g crude drug at 50° C., 60° C., 70° C., and 80° C., stirred for 10 min, cooled, and refrigerated overnight. The extracts were taken out and filtered. The filtration time of the samples was recorded, the clarification condition of the filtrate was observed, and the content and light transmittance rate of total solids and total free amino acids of the filtrate were detected. The results are shown in table 26.

TABLE 26

| Investigation results of clarifying temperature (n = 2) | | | | | |
|---|---|---|---|---|---|
| Clarifying temperature (° C.) | Filtering time (min) | Condition of Clarification | Yield of total solids (%) | Yield of total free amino acids (%) | Transmit-tance rate (%) |
| 50 | 1 | *** | 14.86 | 6.42 | 76.81 |
| 60 | 1 | *** | 14.74 | 6.54 | 86.68 |
| 70 | 1 | *** | 15.17 | 6.54 | 83.56 |
| 80 | 2 | *** | 15.14 | 6.73 | 73.74 |

Note:
1 The clarification effect is expressed by clarification (*), relatively clarification (), turbidity (*); and
2. The suction bottle, Buchner funnel and filter materials used for filtering each group of samples are of the same model and specification.

The results showed that, the clarifying temperature had no significant effect on the yield of water-soluble total solids and total free amino acids. When being clarified at the temperature of 60° C.-70° C., the filtration time of the sample is the shortest, and the light transmittance rate of the filtrate exceeds 80%. Therefore, the clarifying temperature is selected as 60° C.-70° C.

7) Investigation on Heat Treatment and Refrigeration Process

① Investigation of Heat Treatment Process 4 portions of thin extractums were weighed, added with water to prepare solutions with crude drug concentrations of ⅓ g/ml respectively, and well mixed. 2 portions were boiled for 10 min, slowly added with a clarifying agent of 0.6 ml/g crude drug at 70° C. respectively, stirred for 10 min, cooled, and refrigerated overnight. The extracts were taken out and filtered. The filtration time of the samples was recorded, the clarification condition of the filtrate was observed, and the content and light transmittance of total solids and total free amino acids of the filtrate were detected. The results are shown in table 27.

TABLE 27

| Investigation results of process (n = 2) | | | | |
|---|---|---|---|---|
| Boiling or not | Filtering time (min) | Condition of Clarification | Yield of total solids (%) | Yield of total free amino acids (%) |
| Yes | 8.5 | *** | 14.30 | 6.93 |
| No | 15.5 | *** | 14.73 | 6.91 |

Note:
1 The clarification effect is expressed by clarification (*), relatively clarification (), turbidity (*); and
2. The suction bottle, Buchner funnel and filter materials used for filtering each group of samples are of the same model and specification.

The results show that, whether to conduct heat treatment and refrigeration process has no significant effect on the yield of water-soluble total solids and total free amino acids. However, the samples subjected to heat treatment and refrigeration process are easier to be filtered. Therefore, the boiling step is added, and the influence of boiling sequence on filtering.

② Investigation of Boiling Sequence 2 portions of thin extractums were weighed, added with water to prepare solutions with crude drug concentrations of ⅓ g/ml respectively, and well mixed. One portion was boiled for 10 min, cooled to 60° C., slowly added with a clarifying agent of 0.6 ml/g crude drug, and stirred for 10 min. another one portion was slowly added with a clarifying agent of 0.6 ml/g crude drug at 60° C., stirred for 10 min, boiled for 10 min, cooled, refrigerated overnight. The two portions were taken out and filtered. The filtration time of the samples was recorded, the clarification condition of the filtrate was observed, and the content and light transmittance rate of total solids and total free amino acids of the filtrate were detected. The results are shown in table 28.

TABLE 28

| Investigation results of heat treatment sequence (n = 1) | | | | | |
|---|---|---|---|---|---|
| Sample No. | Sequence | Filtering time (mm) | Condition of Clarification | Yield of total solids (%) | Yield of total free amino acids (%) | Transmittance rate (%) |
| Sample 1 | First boiling and then clarifying | 2 | *** | 15.22 | 6.86 | 79.92 |
| Sample 2 | First clarifying and then boiling | 5 | *** | 15.45 | 6.71 | 86.55 |

Note:
1 The clarification effect is expressed by clarification (*), relatively clarification (), turbidity (*); and
2. The suction bottle, Buchner funnel and filter materials used for filtering each group of samples are of the same model and specification.

The results show that, the boiling sequence had no significant effect on the yield of water-soluble total solids and total free amino acids. Moreover, the clarification of filtrate is similar. The sample that is boiled first and then clarified has a faster filtration speed. Considering that, in actual production, it will be more smooth if it is firstly heated, boiled, then cooled to 60-70° C. for clarification, then cooled down, and refrigerated. Therefore, the sequence of boiling first and then cooling down to 60-70° C. for clarification is selected.

③ Investigation of Boiling Time

An appropriate amount of thin extractums was weighed, added with water to prepare a solution with crude drug concentration of ⅓ g/ml, well mixed, divided it into 6 portions, boiled for 10 min, 30 min and 60 min respectively, added for the second and third times, and filtered. The filtrates were combined and cooled. Ethanol was recovered at 65° C. under reduced pressure. The filtrate was concentrated to a relative density of 1.06 (60° C.), added with water to 6000 ml, boiled for 10 min, cooled down to 70° C., slowly added with 600 ml clarifying agent, stirred for 10 min, cooled, divided into 16 portions, refrigerated at 1° C. and 8° C. respectively, taken out at 16 h, 24 h, 40 h, and 48 h respectively, and filtered. The filtration time of the samples and the clarification condition of the filtrate were recorded, and the content of total solids, total free amino acids and light transmittance rate were detected in the filtrates. The results are shown in Table 30.

TABLE 30

| Investigation results of clarification and refrigeration time and refrigeration temperature of clarified liquid (n = 2) | | | | | | |
|---|---|---|---|---|---|---|
| Time | Temperature | Filtering time (min) | Clarification | Transmittance rate | Yield of total solids (%) | Yield of total free amino acids (%) |
| 16 h | 1° C. | 2 | *** | 85.12 | 14.23 | 6.58 |
| | 8° C. | 2 | *** | 71.76 | 14.29 | 6.77 |
| 24 h | 1° C. | 2 | *** | 81.07 | 14.63 | 6.78 |
| | 8° C. | 2 | *** | 78.19 | 14.98 | 6.91 |
| 40 h | 1° C. | 2 | *** | 88.98 | 14.58 | 6.88 |
| | 8° C. | 2 | *** | 80.78 | 14.48 | 6.78 |
| 48 h | 1° C. | 2 | *** | 84.95 | 14.77 | 7.03 |
| | 8° C. | 2 | *** | 80.53 | 14.59 | 6.65 |
| RSD % | / | / | / | 6.38 | 1.67 | 2.11 |

Note:
1 The clarification effect is expressed by clarification (*), relatively clarification (), turbidity (*); and
2. The suction bottle, Buchner funnel and filter materials used for filtering each group of samples are of the same model and specification.

cooled down to 70° C., slowly added with a clarifying agent of 0.6 ml/g crude drug, stirred for 10 min, cooled, refrigerated overnight, taken out, and filtered. The filtration time of the sample and the clarification condition of the filtrate were recorded. The results are shown in Table 29.

TABLE 29

| Investigation results of boiling time (n = 2) | | |
|---|---|---|
| Boiling time (min) | Filtering time (min) | Condition of Clarification |
| 10 | 7.5 | *** |
| 30 | 10.5 | *** |
| 60 | 18 | *** |

Note:
1 The clarification effect is expressed by clarification (*), relatively clarification (), turbidity (*); and
2. The suction bottle, Buchner funnel and filter materials used for filtering each group of samples are of the same model and specification.

The results show that, with the increase of the boiling time, the filtration time increases slightly. Therefore, it will be more appropriate to control the boiling time at 10-30 min 8) Determination of Clarification and Refrigeration Temperature and Refrigeration Time 2000 g Fresh body of *Periplaneta americana* L. was weighed, placed in a glass bottle, added with 1.5 BV of 25% ethanol, sealed, left to stand for 36 days at 40° C., taken out, reflux extracted with 80% ethanol for three times, in which each extraction was performed for 1 h, 1.5 BV of ethanol was added for the first extraction, and 3.0 BV of ethanol was added for the second and third times, and filtered. The filtrates were combined and cooled. Ethanol was recovered at 65° C. under reduced pressure. The filtrate was concentrated to a relative density of 1.05 (60° C.), added with water to 3000 ml, boiled for 10 min, cooled down to 70° C., slowly added with 600 ml clarifying agent, stirred for 10 min, cooled, refrigerated overnight, and filtered. The filtration time of the samples and the clarification condition of the filtrate were recorded, and the content of total solids, total free amino acids and light transmittance rate were detected in the filtrates. The results are shown in Table 31.

The results show that, the refrigeration time and temperature had no effect on the filtration time, clarification, yields of total solids and total free amino acid of the samples. The light transmittance rate of refrigerated samples in the 1° C. group is slightly higher than that in the 8° C. group. According to actual production situation, it is selected to stand the clarified solution stand at 1° C.-8° C. for 16 h-48 h.

9) Clarification Process Repeating Test

Fresh body of *Periplaneta americana* L. was weighed, 1000 g/portion, placed in a glass bottle, added with 1500 ml of 25% ethanol, sealed, left to stand for 20 days at 40° C., taken out, reflux extracted with 80% ethanol for three times, in which each extraction was performed for 1 h, 1.5 BV (1.5 L) of ethanol was added for the first extraction, and 3.0 BV (3.0 L) of ethanol was added for the second and third times,

TABLE 31

| Validation results of clarification process (n = 2) | | | |
| --- | --- | --- | --- |
| Evaluation indexes | Extraction solution | Clarifying solution | Conversion ratio |
| Filtering time (min) | / | 23 | / |
| Clarification | / | *** | / |
| Transmittance (%) | / | 84.08 | / |
| Yield of total solids (%) | 16.36 | 14.78 | 90.34 |
| Yield of total free amino acids (%) | 7.31 | 6.99 | 95.62 |
| Yield of total amino acids (%) | 8.89 | 8.88 | 99.89 |

Clarification effect: clarification (*), relatively clarification (), turbidity (*)

The repeated test results show that the clarification effect is good and the filtration is smooth. The conversion ratios of water-soluble total solids, total free amino acids and total amino acids are more than 90%.

10) Preparation Forming Process (1) Preparation Forming Process Description

An appropriate amount of *Periplaneta americana* L. clarified solution (equivalent to 200 g crude drug) was weighed, added with 150 g glycerol and 1 g potassium sorbate, added with water to 1000 ml, well mixed, filtered (0.22 μm-0.45 μm microporous filter membrane), bottled, sterilized at 116° C.±2° C. for 40 minutes, cooled, inspected, labeled, packaged, and inspected to obtain the finished product.

(2) Selection of Sterilization Methods

The mixture usually adopts wet heat sterilization method. The wet heat sterilization condition under the sterilization method of 1421 in the 2015 edition of Chinese pharmacopoeia usually adopts a program of 121° C.×15 min, 121° C.×30 min or 116° C.×40 min. Considering actual production, the sterilization condition for this preparation was selected as 116° C.±2° C.×40 min. At the same time, the differences of properties, pH value, relative density and total free amino acid content of samples before and after sterilization were compared.

An appropriate amount of clarified solution (equivalent to 80 g crude drug) was weighed, added with 60 g glycerol and 0.4 g potassium sorbate, added with water to 400 ml, well mixed, filtered, and bottled. Half of the samples were sterilized at 116° C. for 40 minutes, taken out, and cooled. Samples were taken respectively to observe properties, and the pH value, relative density and total free amino acid content of the samples were measured. The results are shown in table 32.

TABLE 32

| Inspection results of samples before and after sterilization (n = 2) | | | | |
| --- | --- | --- | --- | --- |
| | Properties | pH value | Relative density | Content of total free amino acids (mg/ml) |
| Sterilized group | Brown clear liquid, slightly fishy and sweet | 5.9 | 1.05 | 16.45 |

TABLE 32-continued

| Inspection results of samples before and after sterilization (n = 2) | | | | |
| --- | --- | --- | --- | --- |
| | Properties | pH value | Relative density | Content of total free amino acids (mg/ml) |
| Unsterilized group | Brown clear liquid, slightly fishy and sweet | 5.9 | 1.05 | 16.36 |

Note:
the color of the sample in the sterilized group is slightly darker than that in the unsterilized group.

The test results show that, the sterilization process has no significant difference in the properties, pH value, relative density and total free amino acids of the samples before and after sterilization.

(3) Forming Process Repeating Test

Fresh body of *Periplaneta americana* L. was weighed, 1000 g/portion, placed in a glass bottle, added with 1500 ml of 25% ethanol, sealed, left to stand for 20 days at 40° C., taken out, reflux extracted with 80% ethanol for three times, in which each extraction was performed for 1 h, 1.5 BV (1.5 L) of ethanol was added for the first extraction, and 3.0 BV (3.0 L) of ethanol was added for the second and third times, and filtered. The filtrates were combined and cooled. Ethanol was recovered at 65° C. under reduced pressure. The filtrate was concentrated to a relative density of 1.06 (60° C.), cooled, added with water to 3000 ml, well mixed, boiled for 10 min, cooled to 70° C., and added slowly with 600 m Clarifying agent, then stirred 10 min, cooled, refrigerated overnight, and filtered to obtain a clear solution of the fresh body of *Periplaneta americana* L. An appropriate amount of clarified solution (equivalent to 200 g fresh body) was weighed, added with 1.0 g potassium sorbate and 150 g glycerol, well mixed, added with water to 1000 ml, well mixed, filtered, bottled by 10 ml/bottle, and sterilized at 115° C. for 40 minutes.

(4) Pharmacodynamic Test Results of Small-Scale Test Samples

1) Preparation of Pharmacodynamic Samples

Fresh body of *Periplaneta americana* L. was weighed, 1000 g/portion, placed in a glass bottle, added with 1500 ml of 25% ethanol, sealed, left to stand for 20 days at 40° C., taken out, reflux extracted with 80% ethanol for three times, in which each extraction was performed for 1 h, 1.5 BV (1.5 L) of ethanol was added for the first extraction, and 3.0 BV (3.0 L) of ethanol was added for the second and third times, and filtered. The filtrates were combined. Ethanol was recovered at 65° C. under reduced pressure. The filtrate was concentrated to a relative density of 1.04 (measured at 60° C.), added with water to 3000 ml, well mixed, boiled for 10 min, cooled to 70° C., slowly added with 600 ml of clarifying agent, stirred for 10 min, cooled, refrigerated overnight, and filtered to obtain a clear solution of the fresh body of *Periplaneta americana* L. 610 ml of clarified solution (equivalent to 200 g fresh body) was weighed, added with 1.0 g potassium sorbate and 150 g glycerol, well mixed, added with water to 1000 ml, well mixed, filtered, bottled by 10 ml/bottle, and sterilized at 115° C. for 40 minutes. The small-scaled samples have a name/code of GD-N1901 and a batch No. 190801.

2) Pharmacodynamic Test Results

40 Gy X-ray was used to irradiate the left cheek pouch of golden hamster (irradiation area: 1.82 cm²). After the onset of oral mucositis, 40 animals with a score of 1-2 were randomly divided into 4 groups (one model control group, and three drug treatment groups) according to the score of oral mucositis (auxiliary reference index: animal weight). Then, the corresponding drugs were administered by intra-peritoneal injection or infiltration of the affected area combined with intragastric administration for 14 days (D12-D25, bid). The dosage is shown in table 33. Through the detection of animal oral mucositis score (modified Sonis score), the therapeutic effect of the tested drugs on radiation oral mucositis in hamsters was evaluated. The results are shown in table 34.

TABLE 33

| | | | | | Administer |
| | | Administration | | Dosage | frequency and |
| Groups | Drugs | route | Dosage/times | volume/times | time |
| --- | --- | --- | --- | --- | --- |
| Model control group | Sterilized water for injection | Infiltration of affected area combined with gastric perfusion | — | 5.4 mL/kg | Bid, 14 d |
| Odkin treatment group | Deproteinized calf serum injection | Intraperitoneal injection | 40 mg/kg | 1 mL/kg | Bid, 14 d |
| Gd-n1901 low dosage group | GD-N1901 | Infiltration of affected area combined with gastric perfusion | 0.27 g/ kg | 5.4 mL/kg | Bid, 14 d |
| Gd-n1901 high dosage group | GD-N1901 | Infiltration of affected area combined with gastric perfusion | 0.54 g/ kg | 5.4 mL/kg | Bid, 14 d |

Note:
10% of the total volume of a given dosage of an animal is infiltrated into the cheek pouch of the irradiated side of the animal, and the remaining 90% is administered by infiltration; and the modeling day is defined as day 0 (day0, D0).

TABLE 34

Hamster Sonis scoring (sores)

| | Groups | | | |
| --- | --- | --- | --- | --- |
| Time | Model control group | Odkin treatment group | low dosage group | high dosage group |
| --- | --- | --- | --- | --- |
| D 12 | 1.35 ± 0.34 | 1.35 ± 0.34 | 1.45 ± 0.37 | 1.35 ± 0.34 |
| D 14 | 2.40 ± 0.39 | 2.25 ± 0.54 | 2.25 ± 0.35 | 2.25 ± 0.54 |
| D 16 | 3.85 ± 0.47 | 3.60 ± 0.39 | 3.50 ± 0.24 | 3.70 ± 0.59 |
| D 18 | 4.20 ± 0.35 | 3.85 ± 0.47 | 3.95 ± 0.28 | 4.00 ± 0.00 |
| D 20 | 3.80 ± 0.26 | 3.50 ± 0.41 | 3.35 ± 0.41* | 3.45 ± 0.16* |
| D 22 | 3.55 ± 0.28 | 3.25 ± 0.49 | 2.85 ± 0.78* | 3.15 ± 0.34* |
| D 24 | 3.35 ± 0.34 | 2.75 ± 0.86 | 2.45 ± 1.04* | 2.70 ± 0.42* |
| D 26 | 2.80 ± 0.48 | 2.00 ± 1.05 | 1.85 ± 1.36 | 2.25 ± 0.75 |

Note:
*stands for $P < 0.05$, compared with the model control group; all data in each group were from 10 animals (n = 10); and the day of modeling is D 0, D 12 represents the 12th day after modeling (the first day of administration), and the rest are similar.

The ulcer onset period of oral mucositis in golden hamsters was 12-18 days after modeling. The score of oral mucositis increased rapidly, and D18 reached the peak (4 points). From the 20th to 26th days (D20 to D26) after modeling, the ulcer was in the recovery period, and the oral mucositis score of animals in various groups continued to decline steadily. After the drug intervention, the oral mucositis score of the model control group (model) animals had been in the highest state from 2 days of administration to the end of the test (D14~D26). The oral mucositis score of the Odkin treatment group, high-dosage group and low-dosage group had been lower than that of the model control group. The low-dosage group has the lowest score and the best recovery during the whole recovery period. From D20 to 24, the scores of oral mucositis in low and high dosage groups were significantly lower than those in model group and model control group (P<0.05). The results showed that low and high dosages of samples could significantly promote the recovery of oral mucositis in hamsters.

The invention claimed is:

1. A method for preparing a formulation containing a *Periplaneta americana* L. extract,
   wherein the method comprises:
      preparing the *Periplaneta americana* L. extract by the following steps:
         a) soaking fresh *Periplaneta americana* L. in ethanol, wherein the concentration of ethanol for soaking is 20%-45%, the time for soaking is 10-60 days and the temperature for soaking is 30° C.-50° C.;
         b) reflux extracting with ethanol to obtain a reflux extract, and filtering the reflux extract to obtain a the filtrate;
         c) concentrating the filtrate into an extractum, and
         d) recovering the extractum as the *Periplaneta americana* L. extract, and
      adding water to the *Periplaneta americana* L. extract in the step d), well mixing, heating and boiling, cooling down to 60° C.~70° C., slowly adding a clarifying agent,
   wherein the clarifying agent is a composition of chitosan and gelatin, stirring, cooling, refrigerating overnight and filtering to obtain a clear solution, and
   wherein the method is carried out without freezing the fresh *Periplaneta americana* L.

2. The method according to claim 1, wherein the time for soaking in step a) is 20-60 days.

3. The method according to claim 1, wherein the temperature for soaking in step a) is 40° C.

4. The method according to claim 1, wherein the amount of ethanol in step a) is 1.5-3.5 times the weight of fresh *Periplaneta americana* L.

5. The method according to claim 1, wherein the concentration of ethanol added in step b) is 50%-80%.

6. The method according to claim 1, wherein the amount of ethanol added in step b) is 1.5-3.5 times the weight of fresh *Periplaneta americana* L.

7. The method according to claim 1, wherein the times for reflux in step b) is 1-3 times; the amount of ethanol added for the first reflux is 1.5 times the weight of fresh *Periplan-*

*eta americana* L.; and the amount of ethanol added for the second or third reflux is three times the weight of fresh *Periplaneta americana* L.

8. The method according to claim 1, wherein the time for reflux in step b) is 1-2 h.

9. The method according to claim 1, wherein the concentrating in step c) is conducted by reduced pressure.

10. The method according to claim 9, wherein the temperature for the concentrating by the reduced pressure in step c) is 60° C.-90° C.

11. The method according to claim 1, wherein the relative density of the extractum in step c) at 60° C. is 1.04-1.08.

12. The method according to claim 1, wherein the content of free amino acids in the *Periplaneta americana* L. extract is 30-55%.

13. The method according to claim 1, wherein the ratio of chitosan to gelatin is 1:1-1:4.

14. The method according to claim 1, wherein the formulation further comprises a sweetener and a preservative.

15. The method according to claim 14, wherein the sweetener is glycerol, cyclamate, aspartame or stevioside; the preservative is hydroxyphenylalkyl esters, benzoic acid, sodium benzoate, sorbic acid or potassium sorbate.

16. The method according to claim 1, wherein the formulation is prepared as a traditional Chinese medicine mixture.

17. The method according to claim 1, wherein the method comprises: after diluting the *Periplaneta americana* L. extract with the water, heating to 100° C., cooling to 70° C., adding the clarifying agent under stirring, refrigerating, filtering, adding glycerol and potassium sorbate to the filtrate, finally adding the remaining water, well mixing, filtering through a microporous filter membrane and sterilizing.

18. The method according to claim 1, wherein the method comprises: weighing fresh body of *Periplaneta americana* L., adding 25% ethanol 1.5 times the weight of the fresh body, sealing, standing at 40° C. for 20 days, taking out, reflux extracting with 80% ethanol for three times, wherein each extraction is performed for 1 h, 1.5BV is added for the first extraction, 3.0 BV is added for the second and third extractions, filtering and obtaining the filtrate, recovering ethanol under reduced pressure at 65° C. and concentrating to a relative density of 1.04 (measured at 60° C.), adding water to 3 times the weight of fresh insects, well mixing, heating and boiling for 10 min, cooling down to 70° C., slowly adding the clarifying agent, stirring, cooling, refrigerating overnight and filtering to obtain a clear solution of the fresh body of *Periplaneta americana* L.; then adding potassium sorbate and glycerol, well mixing, adding water, well mixing, filtering, and sterilizing at 115° C. for 40 min.

19. The method according to claim 1, wherein the concentration of ethanol for soaking in step a) is 25%.

20. The method according to claim 2, wherein the time for soaking in step a) is 20-40 days.

21. The method according to claim 5, wherein the concentration of ethanol added in step b) is 80%.

22. The method according to claim 6, wherein the amount of ethanol added in step b) is 1.5 times the weight of fresh *Periplaneta americana* L.

23. The method according to claim 1, wherein the chitosan is 1% chitosan solution; and gelatin is 1% gelatin solution.

24. The method according to claim 1, wherein the ratio of chitosan to gelatin is 1:3-1:4.

25. The method according to claim 24, wherein the ratio of chitosan to gelatin is 1:3.

26. The method according to claim 14, wherein the amount of the sweetener is 5-20%; and the amount of preservative is 0.05-0.3%.

27. The method according to claim 15, wherein the sweetener is glycerol; the preservative is potassium sorbate.

28. The method according to claim 1, wherein a concentration of a crude drug in the step of adding the clarifying agent is 1/3-1/11 g/ml, wherein the crude drug is the fresh *Periplaneta americana* L.

29. The method according to claim 28, wherein the concentration of the crude drug in the step of adding the clarifying agent is 1/3-1/7 g/ml.

30. The method according to claim 29, wherein the concentration of the crude drug in the step of adding the clarifying agent is 1/3 g/ml.

31. The method according to claim 1, wherein the amount of the clarifying agent in the formulation is 0.2-1.0 ml/g crude drug.

32. The method according to claim 31, wherein the amount of the clarifying agent in the formulation is 0.2-0.6 ml/g crude drug.

33. The method according to claim 1, wherein the reflux extracting is carried out directly after the soaking.

34. The method according to claim 1, wherein the *Periplaneta americana* L. extract by a process consisting essentially of the steps a) through d).

* * * * *